United States Patent
Majeed et al.

(10) Patent No.: US 11,351,102 B2
(45) Date of Patent: Jun. 7, 2022

(54) PLANT ACTIVES AND THEIR ANTI-POLLUTION EFFECTS THEREOF

(71) Applicants: Muhammed Majeed, Bangalore (IN); Kalyanam Nagabhushanam, East Windsor, NJ (US); Lakshmi Mundkur, Bangalore (IN)

(72) Inventors: Muhammed Majeed, Bangalore (IN); Kalyanam Nagabhushanam, East Windsor, NJ (US); Lakshmi Mundkur, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 0 days.

(21) Appl. No.: 17/003,760

(22) Filed: Aug. 26, 2020

(65) Prior Publication Data

US 2021/0059919 A1    Mar. 4, 2021

Related U.S. Application Data

(60) Provisional application No. 62/891,913, filed on Aug. 26, 2019.

(51) Int. Cl.
| | |
|---|---|
| A61K 8/49 | (2006.01) |
| A61K 8/34 | (2006.01) |
| A61K 8/35 | (2006.01) |
| A61K 8/60 | (2006.01) |
| A61Q 17/04 | (2006.01) |
| A61Q 19/10 | (2006.01) |
| A61K 8/365 | (2006.01) |

(52) U.S. Cl.
CPC ............ *A61K 8/498* (2013.01); *A61K 8/347* (2013.01); *A61K 8/35* (2013.01); *A61K 8/365* (2013.01); *A61K 8/602* (2013.01); *A61Q 17/04* (2013.01); *A61Q 19/10* (2013.01); *A61K 2800/10* (2013.01); *A61K 2800/522* (2013.01)

(58) Field of Classification Search
CPC ........ A61K 8/498; A61K 8/602; A61K 8/347; A61K 8/365; A61K 8/35; A61K 2800/10; A61K 2800/522; A61K 2800/5922; A61Q 17/00; A61Q 19/10; A61Q 17/04

See application file for complete search history.

(56) References Cited

U.S. PATENT DOCUMENTS

| | | | |
|---|---|---|---|
| 2011/0033565 A1* | 2/2011 | Majeed | A61K 31/366 424/769 |
| 2016/0287505 A1* | 10/2016 | Rana | A61P 17/00 |
| 2018/0344788 A1* | 12/2018 | Majeed | A61K 36/185 |

OTHER PUBLICATIONS

Abozaid et al. "Chrysin regulates NAD(P)H: quinoneoxidoreductase 1 and inflammatory mediators in rats exposed to smoking and thioacetamide." Benha Veterinary Medical Journal, Mar. 2018, 34(1): 277-288. (Year: 2018).*
Lee et al. "Anti-allergic Effect of Oroxylin A from Oroxylum indicum Using in vivo and in vitro Experiments." Biomol Ther., 2016, 24(3): 283-290. (Year: 2016).*
Oh et al. "Baicalein Protects Human Skin Cells against Ultraviolet B-Induced Oxidative Stress." Biomol Ther, 2016, 24(6): 616-622. (Year: 2016).*
Zhao et al. "Antimelanogenic Effect of an Oroxylum indicum Seed Extract by Suppression of MITF Expression through Activation of MAPK Signaling Protein." Int. J. Mol. Sci., 2018, 19(760): 1-11. (Year: 2018).*

* cited by examiner

*Primary Examiner* — Doan T Phan

(57) ABSTRACT

The present invention discloses a method for protecting mammalian skin against the harmful effects of UV radiation and environmental pollutants, using one or plant actives selected from group comprising a composition comprising not less than 10% w/w oroxylin A, not less than 10% w/w baicalein and not less than 2% w/w chrysin; 95% w/w oxyresveratrol; 95% w/w tetrahydrocurcumin; 90% w/w pterostilbene and a composition comprising at least 10% w/w β-glucogallin and at least 10% w/w total mucic acid gallates. The invention also discloses a method for cleansing and rejuvenating mammalian skin, exposed to environmental pollutants and UV radiation using the aforesaid plant actives.

18 Claims, 12 Drawing Sheets

PLANT ACTIVES AND THEIR ANTI-POLLUTION EFFECTS THEREOF

CROSS-REFERENCE TO RELATED APPLICATION

This is a non-provisional filing claiming priority from U.S. provisional application No. 62/891,913, filed on 26 Aug. 2019, the subject matter of which is incorporated herein by reference.

FILED OF INVENTION

The invention in general pertains to anti-pollution effects of natural bioactive molecules isolated from different plant sources. Specifically, the invention pertains to the use of plant actives for protecting the skin against harmful UV radiation and environmental pollutants.

BACKGROUND OF THE INVENTION

Description of Prior Art

The effect of air pollution on the general health of the population is multi-fold. It affects our daily life by causing several health issues. One of the major effects of these pollutants appears on skin as it causes oxidative damages or interferes with the normal function of cellular proteins, DNA, and Lipids. the skin is exposed to a variety of pollutants thereby causing premature skin ageing, pigmentation spots, or acne or lead to more serious dermatological issues such as atopic dermatitis, psoriasis, and even skin cancer (English, J. S., R. S. Dawe, and J. Ferguson, Environmental effects and skin disease. Br Med Bull, 2003. 68: p. 129-42).

The main sources of pollution include particulate matter, polycyclic aromatic hydrocarbons (PAHs), volatile organic compounds (VOCs), nitrogen and sulfur oxides, carbon monoxide, ozone, and heavy metals (Baudouin, C., et al., Environmental pollutants and skin cancer. Cell Biol Toxicol, 2002. 18 (5): p. 341-8). The toxic gases ($CO_2$, CO, $SO_2$, NO, $NO_2$), low molecular weight hydrocarbons, persistent organic pollutants (e.g., dioxins), heavy metals (e.g., lead, mercury) and particulate matter (PM) form the primary pollutants which are formed from the source. Secondary pollutants, which include ozone ($O_3$), $NO_2$, peroxy acetyl nitrate, hydrogen peroxide and aldehydes are formed in the atmosphere through chemical and photochemical reactions involving primary pollutants (Kampa. M. and E. Castanas, Human health effects of air pollution. Environ Pollut, 2008. 151 (2): p. 362-7). Some environmental pollutants, in which benzo(a)pyrene (BaP) is the major component are potentially hazardous. BaP is identified as class 1 carcinogen by International Agency for Research on Cancer (IARC). BaP gets metabolized into peroxides, quinones, sulphur, and nitric derivatives, which are highly toxic. The main sources of BaP are transport-related emissions (petrol combustion, tarmac, and tire wear, coal and wood). Other sources could be from uncontrolled fires, waste incineration and industrial emissions.

These pollutants coated with carbon particles and PAHs damage the skin and results in skin barrier alteration, oxidative stress, inflammation, and cellular degradation. These pollutants cause several specific skin-related issues, like hyperpigmentation, inflammation, collagen breakdown, elastin breakdown etc. Environmental pollutants like UVA up regulates the formation of matrix metalloproteinase (MMPs), enzymes that degrade the matrix protein's elastin and collagen, which, if not prevented, can result in marked reduction in skin elasticity and increased wrinkling (Risom, L., P. Moller, and S. Loft, Oxidative stress-induced DNA damage by particulate air pollution. Mutat Res, 2005. 592 (1-2): p. 119-37; Moller, P, and S. Loft, Oxidative damage to DNA and lipids as biomarkers of exposure to air pollution. Environ Health Perspect, 2010. 118 (8): p. 1126-36). UVA can penetrate deeper into the skin in comparison to UVB and contributes to photoaging, photocarcinogenesis and photo-dermatosis and increase oxidative stress in fibroblasts and cells which are deeper inside the skin. Blue light (light from mobile, TV, laptop/desktop screens) is reported to exert similar effect (Godley et al., Blue Light Induces Mitochondrial DNA Damage and Free Radical Production in Epithelial Cells. The Journal Of Biological Chemistry, 2005, 280 (22):21061-21066). The effect of different air pollutants on the skin are summarized in the following prior art documents:

a. Araviiskaia et al., The impact of airborne pollution on skin, J Eur Acad Dermatol Venereol. 2019; 33 (8): 1496-1505.
b. Drakaki et al., Air pollution and the skin, Front. Environ. Sci., 2014: 2:1-6
c. Doris Day. The Impact of Pollution on The Skin, HCP live. The Impact of Pollution on The Skin, Source: hcplive.com/view/the-impact-of-pollution-on-the-skin, accessed 20 Aug. 2020.

Anti-pollution products, are believed to prevent the impact of the different air pollutants by:

a. Protecting the skin tissue against harmful reactive oxygen species due to antioxidant activity
b. Reducing inflammation and allergic reaction
c. Help in stopping the cell death that occurs within the skin when exposed to pollutants.

Plant based products are now garnering more attention due to their less toxic nature. Essential oils and extracts of plants like turmeric, coconut, cocoa, basil, onion, green tea, fenugreek, licorice, rosemary, aloe vera etc are used in skin care products. (Aburjai & Natsheh, Plants used in cosmetics, Phytotherapy Research. 2003; 17 (9), 987-1000. doi: 10.1002/ptr.1363). Tetrahydrocurcumin, isolated from *Curcuma longa* is reported from its skin lightening effects (Majeed et al., U.S. Pat. No. 6,653,327). Resveratrol and oxyresveratrol are also well know for the skin care and skin lightening effects. The fruit of *Oroxylum indicum* is also reported to be good for skin and used in the treatment of skin diseases (Chauhan et al., Shyonak, Sona Patha (*Oroxylum indicum*)—Properties, benefits and dosage. Planet Ayurveda, planetayurveda.com/library/shyonak-oroxylum-indicum/, accessed 22 Aug. 2020). *Pterocarpus marsupium* extract, is also reported for its skin lightening and anti-aging effects (Majeed et al., An Open-Label Single-Arm. Monocentric Study Assessing the Efficacy and Safely of Natural Pterostilbene (*Pterocarpus marsupium*) for Skin Brightening and Antiaging Effects, Clin Cosniet Investig Dermatol. 2020; 13: 105-116). However, it is common technical knowledge that not all products used for skin care and skin lightening will be effective is protecting the skin against the harmful pollutants. There still exists an unmet industrial need to find a natural composition comprising one or more bioactive molecules isolated from plants, which confer maximum protection against the harmful pollutants. Further, the composition must be able to protect the skin from the pollutants and also cleanse and rejuvenate the skin exposed to environmental pollutants. The present invention solves the above problem by disclosing a composition comprising one or more bioactive molecules selected from the group comprising of 95% w/w oxyresveratrol; 95% w/w tetrahydrocurcumin; composition comprising at least 10% w/w β-glucogallin and at least 10% w/w total mucic acid gallates and composition comprising not less than 10% w/w oroxylin A, not less than 10% w/w baicalein and not less than 2% w/w chrysin.

The principle object of the invention is to disclose a method for protecting mammalian skin against the harmful effects of UV radiation and environmental pollutants, using a composition comprising one or more ingredients selected from the group consisting of 95% w/w oxyresveratrol; 95% w/w tetrahydrocurcumin; composition comprising at least 10% w/w β-glucogallin and at least 10% w/w total mucic acid gallates and composition comprising not less than 10% w/w oroxylin A, not less than 10% w/w baicalein and not less than 2% w/w chrysin.

It is other object of the invention to disclose a method for cleansing and rejuvenating mammalian skin, exposed to environmental pollutants and UV radiation, using a composition comprising one or more ingredients selected from the group consisting of 95% w/w oxyresveratrol; 95% w/w tetrahydrocurcumin; 90% w/w pterostilbene; composition comprising at least 10% w/w β-glucogallin and at least 10% w/w total mucic acid gallates and composition comprising not less than 10% w/w oroxylin A, not less than 10% w/w baicalein and not less than 2% w/w chrysin.

The present invention fulfils the abovementioned objects and provides further related advantages.

SUMMARY OF THE INVENTION

In a most preferred embodiment, the invention discloses a method for protecting mammalian skin against the harmful effects of UV radiation and environmental pollutants, said method comprising a step of topically administering a composition comprising one or more ingredients selected from the group consisting of a composition comprising not less than 10% w/w oroxylin A, not less than 10% w/w baicalein and not less than 2% w/w chrysin; 95% w/w oxyresveratrol; 95% w/w tetrahydrocurcumin; 90% w/w pterostilbene and a composition comprising at least 10% w/w β-glucogallin and at least 10% w/w total mucic acid gallates to a mammal in need of such protection.

In a most preferred embodiment, the invention discloses a method for cleansing and rejuvenating mammalian skin, exposed to environmental pollutants and UV radiation, said method comprising a step of topically administering a composition comprising one or more ingredients selected from the group consisting of a composition comprising not less than 10% w/w oroxylin A, not less than 10% w/w baicalein and not less than 2% w/w chrysin; 95% w/w oxyresveratrol; 95% w/w tetrahydrocurcumin; 90% w/w pterostilbene and a composition comprising at least 10% w/w β-glucogallin and at least 10% w/w total mucic acid gallates to a mammal in need of such effect.

Other features and advantages of the present invention will become apparent from the following more detailed description, which illustrate, by way of example, the principle of the invention.

DETAILED DESCRIPTION OF PREFERRED EMBODIMENTS

Figure 1:
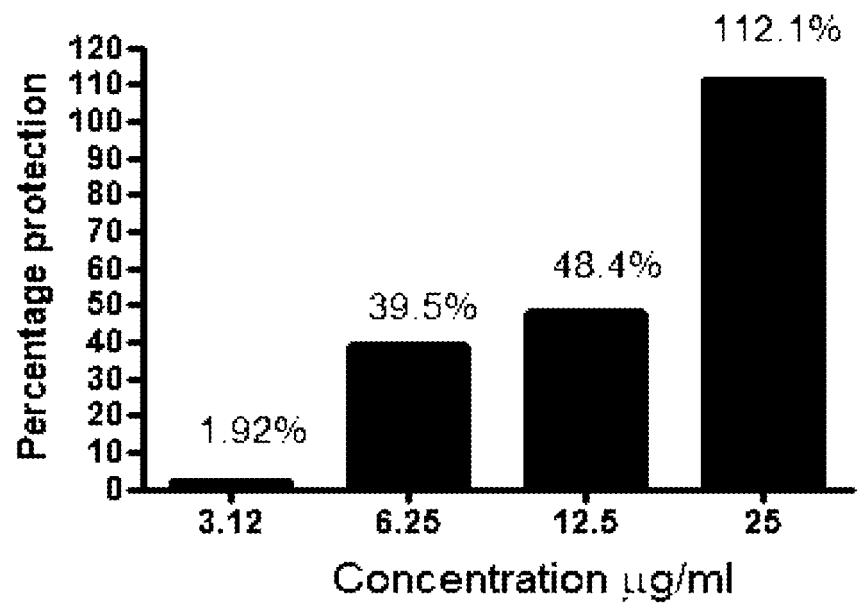
FIG. 1 is a graphical representation showing protection of Human HaCaT keratinocyte cells against UVA and BaP induced damage using a composition comprising oroxylin, baicalein and chrysin.

In a most preferred embodiment, the invention discloses a method for protecting mammalian skin against the harmful effects of UV radiation and environmental pollutants, said method comprising a step of topically administering a composition comprising not less than 10% w/w oroxylin A, not less than 10% w/w baicalein and not less than 2% w/w chrysin to a mammal in need of such protection. In a related embodiment, the composition further comprises one or more ingredients selected from the group consisting of 95% w/w oxyresveratrol; 95% w/w tetrahydrocurcumin; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a method for cleansing and rejuvenating mammalian skin, exposed to environmental pollutants and UV radiation, said method comprising a step of topically administering a composition comprising not less than 10% w/w oroxylin A, not less than 10% w/w baicalein and not less than 2% w/w chrysin to a mammal in need of such effect. In a related embodiment, the composition further comprises one or more ingredients selected from the group consisting of 95% w/w oxyresveratrol; 95% w/w tetrahydrocurcumin; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a composition comprising not less than 10% w/w oroxylin A, not less than 10% w/w baicalein and not less than 2% w/w chrysin for use in protecting mammalian skin against the harmful effects of UV radiation and environmental pollutants. In a related aspect, the invention discloses a composition comprising not less than 10% w/w oroxylin A, not less than 10% w/w baicalein and not less than 2% w/w chrysin for use in for use in cleansing and rejuvenating mammalian skin, exposed to environmental pollutants and UV radiation. In a related embodiment, the composition further comprises one or more ingredients selected from the group consisting of 95% w/w oxyresveratrol; 95% w/w tetrahydrocurcumin; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8. In a related aspect, the composition is formulated with pharmaceutically/cosmeceutically acceptable excipients, adjuvants, bases, diluents, carriers, conditioning agents, antioxidants, bioavailability enhancers, and preservatives and or incorporated into formulations containing skin care ingredients and administered topically in the form of creams, gels, lotions, powder, serum, oil, suspensions, ointments, soaps, scrubs, emulsions, and compacts.

In a most preferred embodiment, the invention discloses a method for protecting mammalian skin against the harmful effects of UV radiation and environmental pollutants, said method comprising a step of topically administering a composition comprising 95% w/w oxyresveratrol to a mammal in need of such protection. In a related embodiment, the composition further comprises one or more ingredients selected from the group consisting of a composition comprising not less than 10% w/w oroxylin A, not less than 10% w/w baicalein and not less than 2% w/w chrysin; 95% w/w tetrahydrocurcumin; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a method for cleansing and rejuvenating mammalian skin, exposed to environmental pollutants and UV radiation, said method comprising a step of topically administering a composition comprising 95% w/w oxyresveratrol to a mammal in need of such effect. In a related embodiment, the composition further comprises one or more ingredients selected from the group consisting of a composition comprising not less than 10% w/w oroxylin A, not less than 10% w/w baicalein and not less than 2% w/w chrysin; 95% w/w tetrahydrocurcumin; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1 alpha, IL-1beta, tumor necrosis factor (TNF)-alpha and IL-8. In another related aspect, the inflammatory marker is IL-8.

In another most preferred embodiment, the invention discloses a composition comprising 95% w/w oxyresveratrol for use in protecting mammalian skin against the harmful effects of UV radiation and environmental pollutants. In a related aspect, the invention discloses a composition comprising 95% w/w oxyresveratrol for use in for use in cleansing and rejuvenating mammalian skin, exposed to environmental pollutants and UV radiation. In a related embodiment, the composition further comprises one or more ingredients selected from the group consisting of composition comprising not less than 10% w/w oroxylin A, not less than 10% w/w baicalein and not less than 2% w/w chrysin, 95% w/w tetrahydrocurcumin; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In a related aspect, the composition is formulated with pharmaceutically/cosmeceutically acceptable excipients, adjuvants, bases, diluents, carriers, conditioning agents, antioxidants, bioavailability enhancers, and preservatives and/or incorporated into formulations containing skin care ingredients and administered topically in the form of creams, gels, lotions, powder, serum, oil, suspensions, ointments, soaps, scrubs, emulsions, and compacts.

In a most preferred embodiment, the invention discloses a method for protecting mammalian skin against the harmful effects of UV radiation and environmental pollutants, said method comprising a step of topically administering a composition comprising 95% w/w tetrahydrocurcumin to a mammal in need of such protection. In a related embodiment, the composition further comprises one or more ingredients selected from the group consisting of composition comprising not less than 10% w/w oroxylin A, not less than 10% w/w baicalein and not less than 2% w/w chrysin; 95% w/w oxyresveratrol; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a method for cleansing and rejuvenating mammalian skin, exposed to environmental pollutants and UV radiation, said method comprising a step of topically administering a composition comprising 95% w/w tetrahydrocurcumin to a mammal in need of such effect. In a related embodiment, the composition further comprises one or more ingredients selected from the group consisting of a composition comprising not less than 10% w/w oroxylin A, not less than 10% w/w baicalein and not less than 2% w/w chrysin; 95% w/w oxyresveratrol; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a composition comprising 95% w/w tetrahydrocurcumin for use in protecting mammalian skin against the harmful effects of UV radiation and environmental pollutants. In a related aspect, the invention discloses a composition comprising 95% w/w tetrahydrocurcumin for use in for use in cleansing and rejuvenating mammalian skin, exposed to environmental pollutants and UV radiation. In a related embodiment, the composition further comprises one or more ingredients selected from the group consisting of composition comprising not less than 10% w/w oroxylin A, not less than 10% w/w baicalein and not less than 2% w/w chrysin, 95% w/w oxyresveratrol; 90% w/w pterostilbene and a composition comprising at least 10% w/w β-glucogallin and at least 10% w/w total mucic acid gallates. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In a related aspect, the composition is formulated with pharmaceutically/cosmeceutically acceptable excipients, adjuvants, bases, diluents, carriers, conditioning agents, antioxidants, bioavailability enhancers, and preservatives and/or incorporated into formulations containing skin care ingredients and administered topically in the form of creams, gels, lotions, powder, serum, oil, suspensions, ointments, soaps, scrubs, emulsions, and compacts.

In a most preferred embodiment, the invention discloses a method for protecting mammalian skin against the harmful effects of UV radiation and environmental pollutants, said method comprising a step of topically administering a composition comprising at least 10% w/w β-glucogallin and at least 10% w/w total mucic acid gallates to a mammal in need of such protection. In a related embodiment, the composition further comprises one or more ingredients selected from the group consisting of composition comprising not less than 10% w/w oroxylin A, not less than 10% w/w baicalein and not less than 2% w/w chrysin; 95% w/w oxyresveratrol; 90% w/w pterostilbene and 95% w/w tetrahydrocurucmin. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a method for cleansing and rejuvenating mammalian skin, exposed to environmental pollutants and UV radiation, said method comprising a step of topically administering a composition comprising at least 10% w/w β-glucogallin and at least 10% w/w total mucic acid gallates to a mammal in need of such effect. In a related embodiment, the composition further comprises one or more ingredients selected from the group consisting of composition comprising not less than 10% w/w oroxylin A, not less than 10% w/w baicalein and not less than 2% w/w chrysin; 95% w/w oxyresveratrol; 90% w/w pterostilbene and 95% w/w tetrahydrocurucmin. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8.

In another most preferred embodiment, the invention discloses a composition comprising at least 10% w/w β-glucogallin and at least 10% w/w total mucic acid gallates for use in protecting mammalian skin against the harmful effects of UV radiation and environmental pollutants. In a related aspect, the invention discloses a composition comprising at least 10% w/w β-glucogallin and at least 10% w/w total mucic acid gallates for use in for use in cleansing and rejuvenating mammalian skin, exposed to environmental pollutants and UV radiation. In a related embodiment, the composition further comprises one or more ingredients selected from the group consisting of composition comprising not less than 10% w/w oroxylin A, not less than 10% w/w baicalein and not less than 2% w/w chrysin, 95% w/w oxyresveratrol; 90% w/w pterostilbene and 95% tetrahydrocurcumin. In another related aspect, the environmental pollutants are selected from the list comprising of, but not limited to, particulate matter, polycyclic aromatic hydrocarbons (PAHs), volatile organic compounds (VOCs), detergents, nitrogen and sulfur oxides, carbon monoxide, ozone, and heavy metals. In yet another related aspect, the composition confers skin protection by decreasing collagenase activity, increasing the levels of anti-oxidant enzymes and decreasing ROS levels and reducing levels of inflammatory markers. In another related aspect, the antioxidant enzymes are selected from the group consisting of glutathione peroxidase, superoxide dismutase and catalase. In another related aspect, the inflammatory markers are selected from the group consisting of interleukin (IL)-1alpha, IL-1beta, tumor necrosis factor (TNF)-alpha and IL-8. In another related aspect, the inflammatory marker is IL-8. In a related aspect, the composition is formulated with pharmaceutically/cosmeceutically acceptable excipients, adjuvants, bases, diluents, carriers, conditioning agents, antioxidants, bioavailability enhancers, and preservatives and/or incorporated into formulations containing skin care ingredients and administered topically in the form of creams, gels, lotions, powder, serum, oil, suspensions, ointments, soaps, scrubs, emulsions, and compacts.

In a related aspect, one or more skin care ingredients are selected from the group consisting of, but not limited to, Alpha Lipoic Acid, Beet root extract, *Boswellia serrata* Extract, β boswellic acids, *Boswellia serrata* oil, *Centella asiatica* Extract, triterpenes, *Garcinia indica* extract, anthocyanins, *Cocos nucifera* extract and juice, *Coleus forskohlii* Extract, forskolin, *Coleus forskohlii* Oil, Tetrahydropiperine, Ellagic Acid, Gallnut Extract, polyphenols, Galanga Extract, Glycyrrhizinic Acid, Green Tea Extract, Epigallocatechin Gallate, Licorice extract, MonoAmmonium Glycyrrhizinate, Limonoids, Oleanolic Acid, Cosmetic peptides (Oleanolic acid linked to Lys-Thr-Thr-Lys-Ser, Oleanolic acid linked to Lys-Val-Lys), Oleuropein, Piper longumine extract, pipeline, Ellagic acid, Pomegranate Extract (Water Soluble), pterostilbene, resveratrol, *Pterocarpus santalinus* extract, Rosemary Extract, Rosmarinic Acid, Amla extract, beta glucogallin, tetrahydrocurcumin, *Salvia officinalis* (Sage) Leaf Extract, Ursolic Acids, Saponins, *Sesamum indicum* (Sesame) Seed Extract, Sesamin and sesamolin, moringa oil, moringa seed extract, Horse Chestnut Extract, Vitex Oil, Xymenynic Acid, ethyl ascorbic acid, Argan oil, Lemon peel extract, turmeric oil, Barley Beta Glucans, coenzyme Q10, olive oil, avocado oil and cranberry oil.

In another related aspect, one or more anti-oxidants and anti-inflammatory agents are selected from the group consisting of, but not limited to, vitamin A, D, E, K, C, B complex, rosmarinic acid, Alpha Lipoic Acid, Ellagic Acid, Glycyrrhizinic Acid, Epigallocatechin Gallate, plant polyphenols, Glabridin, moringa oil, oleanolic acid, Oleuiopein, Camosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosylrutin, catalase and the superoxide dismutase, glutathione, selenium compounds, butylated hydroxyanisole (BHA), butylated hydroxy toluene (BHT), sodium metabisulfite (SMB), propyl gallate (PG) and amino acid cysteine.

In another related aspect, one or more bioavailability enhancers are selected from the group, but not limited to, piperine, tetrahydropiperine, quercetin, Garlic extract, ginger extract, and naringin.

Specific illustrative examples enunciating the most preferred embodiments are included herein below.

EXAMPLES

Example 1: Methodology

Plant Actives

The composition comprising not less than 10% w/w oroxylin A, not less than 10% w/w baicalein and not less than 2% w/w chrysin was obtained from the bark of *Oroxylum indicum* through a process outline in U.S. Pat. No. 10,555,982. The composition is commercially available from Sami Labs Limited as Sabroxy®. The 95% w/w oxyresveratrol was standardised from *Artocarpus lakoocha* using a standardised internal process and it is also commercially available as Artonox® from Sami Labs Limited. The plant active comprising 95% w/w tetrahydrocurcumin was isolated from *Curcuma longa* using a commercially available process and is also available from Sami Labs Limited as Sabiwhite®. The composition comprising at least 10% w/w β-glucogallin and at least 10% w/w total mucic acid gallates was standardised from *Emblica officinalis* and is commercially available as Saberry® from Sami Labs Limited. The 90% w/w pterostilbene composition was isolated and standardised from *Pterocarpus marsupium* using a standardised process and is also commercially available as Pterowhite® from Sami Labs Limited.

ROS Assay

A cell permeable, non-fluorescent dye, 2',7'-dichlorofluorescein diacetate (DCFH-DA) enters the cell and the acetate group on DCFH-DA is cleaved by cellular esterases, trapping the non-fluorescent DCFH inside the cell. Subsequent oxidation by reactive oxygen species generated in the cells, yields the fluorescent DCF which can be detected at 485/520 Ex:Em wavelength. The scavenging activity of sample is indicated by the decrease in fluorescence when compared to the control without antioxidant.

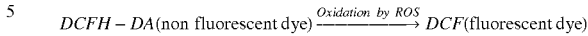

$$DCFH-DA(\text{non fluorescent dye}) \xrightarrow{Oxidation\ by\ ROS} DCF(\text{fluorescent dye})$$

Human HaCaT keratinocyte cells/mouse fibroblast cells were maintained in DMEM containing 25 mM glucose with 10% heat-inactivated fetal calf serum with antibiotics at 37° C. and 5% CO2. When the cells were 70-80% confluent, they were trypsinized, washed and seeded in 96 well plates at a density seeded at a density of 5×104 cells/well. Cells were allowed to adhere for overnight. Cells were pretreated with varying non toxic concentrations of different plant actives for 60 minutes before exposing to the pollutant. Cells were exposed to the following pollutants in the presence of plant actives.

UVA intensity of 15 Joules/m2 for 60 mins,
UV-B intensity of 4.6 Joule/m2 for 10 mins
Heavy metals (Cobalt chloride and Lead Nitrate at 0.25 mm each) for 6 hours Intracellular ROS was determined after the specific treatment period by adding freshly prepared DCFH-DA reagent to all the wells at a concentration of 10 µg/well and incubated at 37° C. for 30 mins. The fluorescence was recorded at a wavelength of 485:520 (Ex:Em) nm in BMG FluoStar Optima microplate reader.

Protection Against Polycyclic Aromatic Hydrocarbons in the Presence of UVA

Polycyclic aromatic hydrocarbons (PAHs) are a class of mutagenic and tumorigenic environmental contaminants. PAHs are widespread in the environment produced from incomplete combustion of natural materials and tobacco smoke (Connell, D. W.; Hawker, D. W.; Warne, M. J.; Vowles. P. P.; Polycyclic aromatic hydrocarbons (PAHs). In Introduction into Environmental Chemistry (McCombs. K., and Starkweather, A. W., eds), 1997, pp. 205-217, CRC Press LLC, Boca Raton, Fla. 2. Shaw, G. R.; Connell, D. W.: Prediction and monitoring of the carcinogenicity of polycyclic aromatic compounds (PACs). Rev. Environ. Contam. Toxic., 1994, 135, 1-62.) PAHs themselves are biologically inert and require metabolic activation. in order to exert genotoxicity PAHs absorb light in the UVA region, react with oxygen or other molecules to generate reactive intermediates (Yu H, Xia Q, Yan J, et al. Photoirradiation of polycyclic aromatic hydrocarbons with UVA light—a pathway leading to the generation of reactive oxygen species, lipid peroxidation, and dna damage. Int J Environ Res Public Health. 2006; 3:348-354) Thus, PAHs can be "activated" by light irradiation to cause photo-induced cytotoxicity. Thus photoirradiation of PAHs with UVA irradiation represents a pollutant which causes cytotoxicity and DNA damage.

Human HaCaT keratinocyte cells were seeded at a density of 1×104 cells/well in 96 well plates. Cells were allowed to adhere for overnight. They were pretreated with Benzo(a) pyrene a PAH at 0.5 mM concentration along with different concentrations of plant actives for 50 minutes, exposed to UVA at an intensity of 17 Joules m2. Cells were washed with sterile buffer and fresh culture medium (2% of FBS) with respective concentrations of plant actives were added followed by incubation for 24 hours at 37° C. in a CO2 incubator. Neutral Red (25 µg/mL) (3-amino-7-dimethyl-amino-2-methylphenazine hydrochloride), was added to the cells for 3 hours. The uptake of NR by the cells was determined by lysing the cells and reading the absorbance at 540 nm in a Tecan microplate reader (TECAN Ltd, Männedorf, Switzerland)

Antioxidant Assay

Cellular anti-oxidants are depleted by pollutants. The ability of plant actives to increase these anti-oxidant enzymes in the cells was studied in vitro. Human HaCaT keratinocyte cells were seeded at a density of 5×105 cells, well in 6 well plates. The cells were pretreated for one hour with plant actives and exposed to UVA intensity of 17 Joules/m2 for 50 mins. Cells were washed with sterile buffer and fresh culture medium (2% of FBS) with respective concentrations of plant actives were added followed by incubation for 24 hours at 37° C. in a CO2 incubator. Cell lysate were prepared and superoxide dismutase (SOD) levels and glutathione peroxidase (GPx) were estimated.

Estimation of Superoxide Dismutase (SOD) Activity

The activity of SOD in the cell lysate was measured by WST-1 method using a kit as per the manufacturer's instructions (Elabsciences). Xanthine Oxidase (XO) can catalyze WST-1 react with O2. —to generate a water-soluble formazan dye. SOD can catalyze the disproportionation of superoxide anions, so the reaction can be inhibited by SOD, and the activity of SOD is negatively correlated with the amount of formazan dye. Therefore, the activity of SOD can be determined by the colorimetric analysis of WST-1 products.

Estimation of Glutathione Peroxidase (GPx) Activity

Glutathione peroxidase activity was determined according to the method of Hafeman et al. (1974). Glutathione peroxidase degrades H2O2 in presence of glutathione (GSH) thereby depleting it. GSH remaining is measured using DTNB, which gives a colored complex.

To a volume of 100 µl of cell lysate, 0.2 mM GSH, 0.05 mM H2O2 and 1 mM NaN3 in a total volume of 250 µl with 1M sodium phosphate buffer (pH 7.0). The reaction was incubated at 37° C. for 10 min and stopped by adding 50 µl of 25% TCA. The reaction mixture was centrifuged at 3000 rpm for 10 min and to 0.1 ml of the supernatant, 0.1 ml of 0.4 M Na2HPO4 and 50 µl of 1 mM DTNB was added. The intensity of yellow color formation was measured at 412 nm after incubation at 37° C. for 10 min The enzyme activity was expressed as units/mg protein.

DPPH-Free Radical Scavenging Assay

Reactive oxygen species (ROS) including superoxide, hydroxyl, peroxyl, and alkoxy radicals are produced by normal metabolic processes. Under normal condition, these free radicals are scavenged by the cellular anti-oxidants and remain in equilibrium. Radiations, toxins and pollutants increase the ROS which can induce oxidative damage to biomolecules such as lipids, nucleic acids, proteins and carbohydrates. These ROS induced damage causes skin irritation, inflammation, ageing, cancer and many other diseases, α, α-diphenyl-β-picrylhydrazyl (DPPH) free radical scavenging method is one of the first approach for evaluating the antioxidant potential of a compound.

Materials

Equipment: Tecan microplate reader (TECAN Ltd. Männedorf, Switzerland)
Reagents: 0.1 mM of DPPH in ethanol, 0.1M phosphate buffered saline (pH 7.4)
Microtitre plates: 96 well microtitre plates (Corning, USA)

Procedure

DPPH is a stable free radical in a methanolic solution with an absorbance at 520 nm. If the free radicals are scavenged by an anti oxidant molecule, the resulting solution appears yellow. The hydrogen atoms or electrons donation ability of the extracellular metabolite was measured by the bleaching of purple coloured DPPH methanol solution.

Different concentrations of various plant actives were diluted in methanol. For the DPPH radical scavenging assay, 20 µL of different concentration of sample was mixed with 180 µL of DPPH in methanol in a 96 well plate following the method as described earlier (Clarke et al., 2013). The plate was kept in the dark for 15 min. after which the absorbance of the solution was measured at 540 nm using a microplate reader (TECAN Ltd, Männedorf. Switzerland). Blanks (DMSO, methanol) and standard (TBHQ solution in methanol) were recorded simultaneously. The extracts were screened with variable concentrations to establish the inhibition concentration (IC50, the concentration reducing DPPH absorbance by 50%).

The free radical scavenging activity was calculated as follows.

$$\% \text{ scavenging activity} = \frac{(B - C) - (S - C)}{(B - C)} \times 100$$

Where,
B=Absorbance of reference solution (OD of DPPH)
C=Absorbance of reference solution blank (OD of Methanol only)
S=Absorbance of test solution
C=Absorbance of test solution blank

Anti-Inflammatory Activity

IL8 in the assay supernatants were measured using Duoset ELISA kit (R & D systems, Cat No. DY208)

Anti-Collagenase Activity

Collagenase is one of the matrix metalloprotease, which digest collagen and other components of the extra cellular matrix (ECM). The ECM serves as a scaffold to stabilize the skin structure, and also helps in proliferation and metabolic functions of the skin cells. Loss of collagen leads to wrinkles and sagging of skin. The principle of the assay of collagenase inhibition is based on the fact that the substrate DQ™ gelatine is conjugated to fluorecein—a fluorescent compound. In DQ™ gelatine, fluorescence is quenched. DQ™ gelatine is efficiently digested by collagenases to yield a fluorescent compound which can be measured. The increase in fluorescence is proportional to enzyme activity. In the presence of an anti-collagenase compound the amount of fluorescence will be decreased for a fixed concentration of enzyme and substrate.

Materials

Equipment—BMG FLUOstar Optima (fluorescent Microplate reader)
Reagents: Phosphate buffer (pH 7.4)
Collagenase Enzyme assay kit (Enzchek® collagenase, gelatinase assay kit, Invitrogen, USA)
Microtitre plates—96 well microtitre plates (black)—Corning, USA.

The assay was performed in a 96 well black microtitre plate. Type IV from *Clostridium histolyticum* with DQ gelatin as substrate was used for the assay. Different concentrations of various plant actives were pre incubated with 20 μl of gelatin substrate (12.5 μg/ml). 100 μl of the Collagenase enzyme solution (final concentration—0.4 U/ml) was added and the fluorescence intensity was measured at Em: 485 nm and Ex: 520 nm after 30 minutes. Enzyme activity of control (buffer) was recorded
The percentage inhibition is calculated as follows:—

$$\% \text{ Inhibition} = \frac{(B - BC) - (T - C)}{(B - BC)} \times 100$$

B—Fluorescence in the presence of enzyme.
BC—Fluorescence in the absence of enzyme activity
T—Fluorescence of enzyme activity in the presence of inhibitor
TC—Fluorescence of the inhibitor alone

Example 2: Anti-Pollution Effects of the Composition Comprising Oxoxylin A, Baicalein and Chrysin

Protection Against UVA and BaP

Figure 2A:
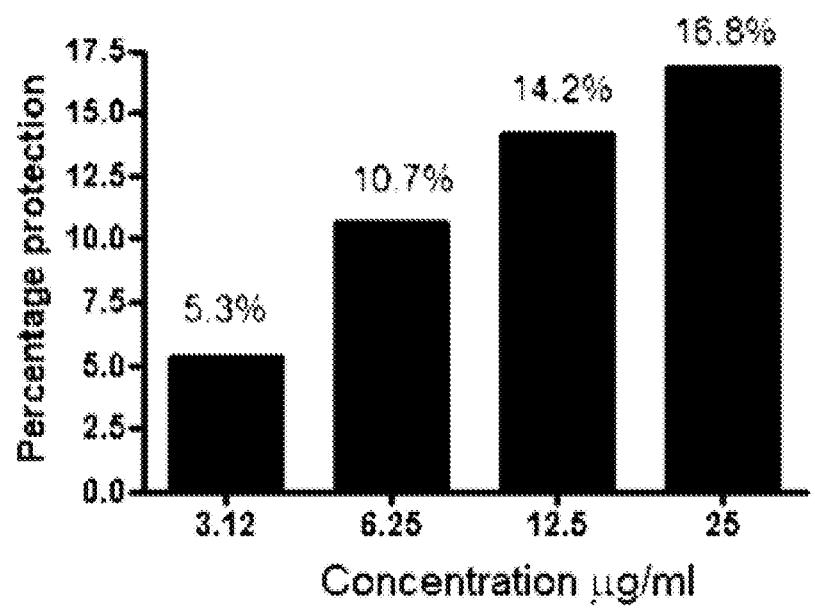
FIG. 2a is a graphical representation showing reduction of ROS induced by heavy metals using a composition comprising oroxylin, baicalein and chrysin.
Figure 2B:
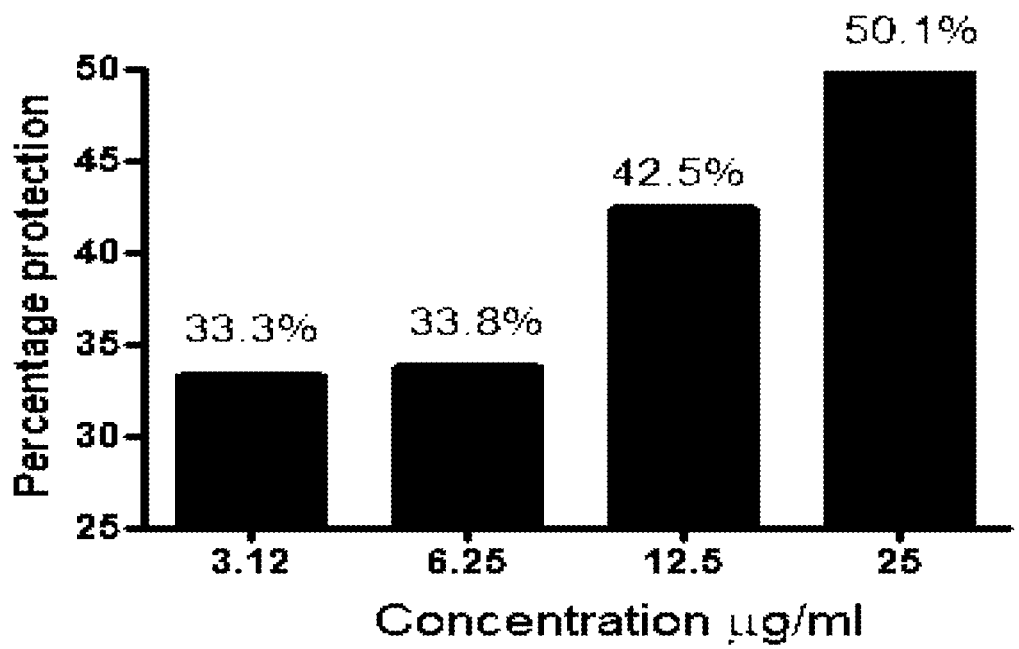
FIG. 2b is a graphical representation showing reduction of UVA-induced ROS using a composition comprising oroxylin, baicalein and chrysin.
Figure 2C:
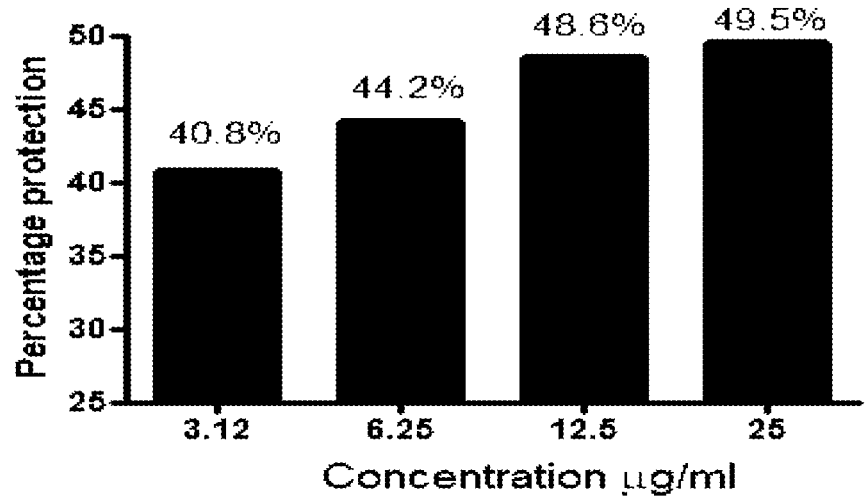
FIG. 2c is a graphical representation showing reduction of UVB-induced ROS using a composition comprising oroxylin, baicalein and chrysin.

The composition comprising oroxylin A, baicalein and chrysin at concentrations of 3.12-25 μg/ml, conferred a dose dependant protection against UVA+BaP (FIG. 1). Similarly, the composition reduced the ROS generated by exposure to heavy metals (FIG. 2a), UVA (FIG. 2b) and UVB (FIG. 2c).

Normalising Antioxidant Enzyme Activity

Figure 3A:
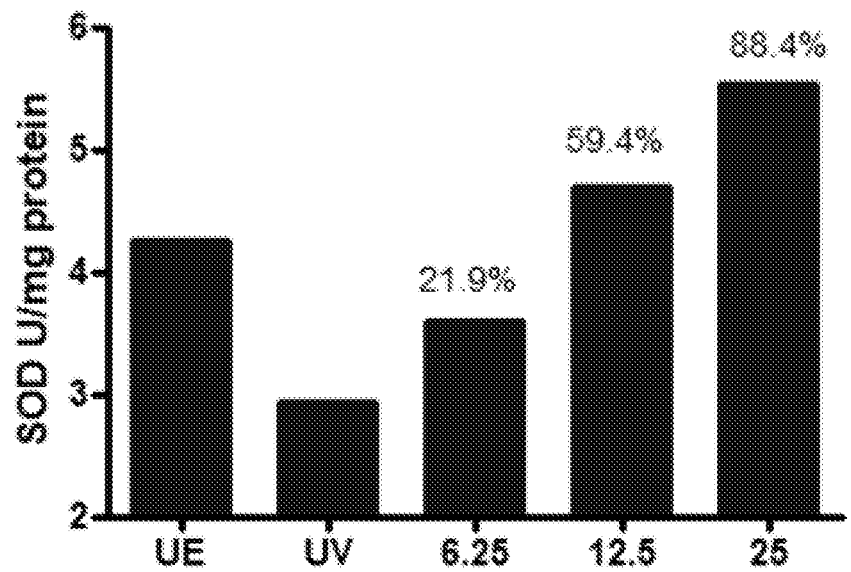
FIG. 3a is a graphical representation showing a dose dependant increase in superoxide dismutase activity by a composition comprising oroxylin, baicalein and chrysin. UE-Unexposed, UV-exposed
Figure 3B:
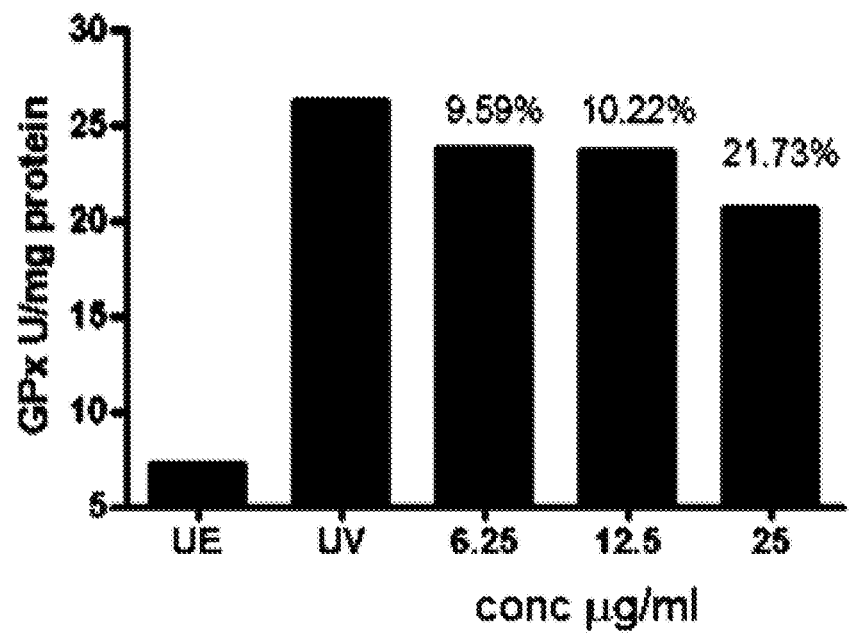
FIG. 3b is a graphical representation showing a dose dependant decrease in glutathione peroxidase activity by a composition comprising oroxylin, baicalein and chrysin. UE-Unexposed, UV-exposed

Exposure to UV reduced the superoxide dismutase concentrations and increased the glutathione peroxidase activity. The composition restored normal enzyme activity in Keratinocytes (FIGS. 3a and 3b)

Inhibition of Inflammatory Cytokines Induced by Pollutants

The composition comprising oroxylin A, baicalein and chrysin inhibited the production of IL-8, which is induced by the pollutants (Table 1)

TABLE 1

Inhibition of IL-8 by the composition comprising oroxylin A, baicalein and chrysin

| Concentration (μg/ml) | % inhibition of IL-8 |
|---|---|
| 12.5 | 6.37 |
| 25.00 | 15.61 |

Antioxidant Activity

The composition comprising oroxylin A, baicalein and chrysin exhibited excelled antioxidant activity by inhibiting the DPPH radical in a dose dependant manner with an IC50 of 5.1 μg/ml (Table 2).

TABLE 2

DPPH radical scavenging activity of the composition comprising oroxylin A, baicalein and chrysin

| Concentration (μg/ml) | % inhibition |
|---|---|
| 50.00 | 95.13 |
| 25.00 | 92.88 |
| 12.50 | 87.28 |
| 6.25 | 56.22 |
| 3.125 | 28.96 |
| IC50 | 5.1 (μg/ml) |

Anti Collagenase Activity

The harmful pollutants damage the skin by degrading collagen. The composition comprising oroxylin A, baicalein and chrysin inhibiting collagen degradation by inhibiting the enzyme collagenase (Table 3)

TABLE 3

Anti-collagenase activity composition comprising oroxylin A, baicalein and chrysin

| Concentration (μg/ml) | % inhibition |
|---|---|
| 200 | 48.13 |
| 100 | 33.37 |
| 50 | 23.65 |
| 25 | 13.5 |

Example 3: Anti-Pollution Effects of the β-Glucogallin Composition

Protection Against UVA and BaP

Figure 4:
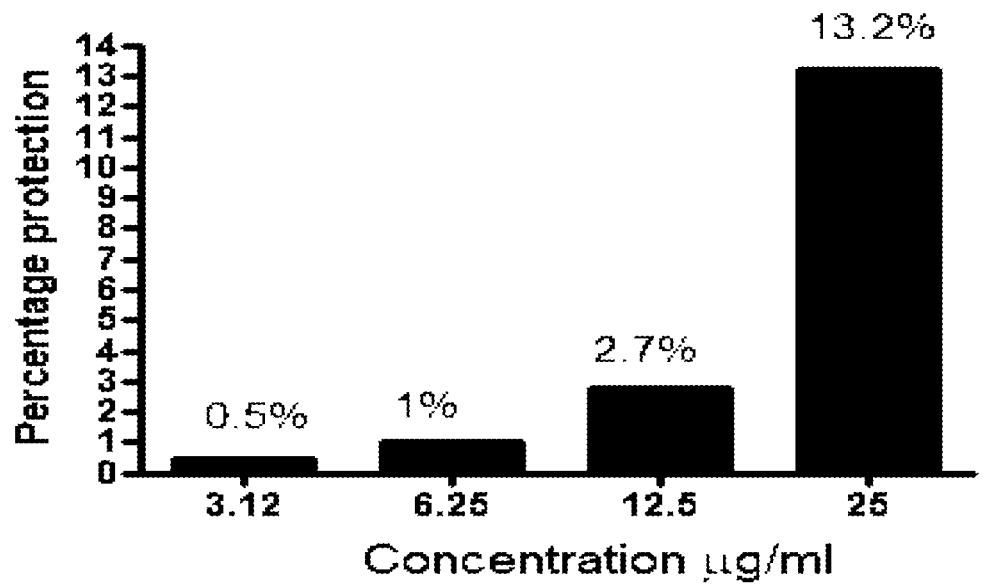
FIG. 4 is a graphical representation showing protection of Human HaCaT keratinocyte cells against UVA and BaP induced damage using a composition comprising β-glucogallin.
Figure 5A:
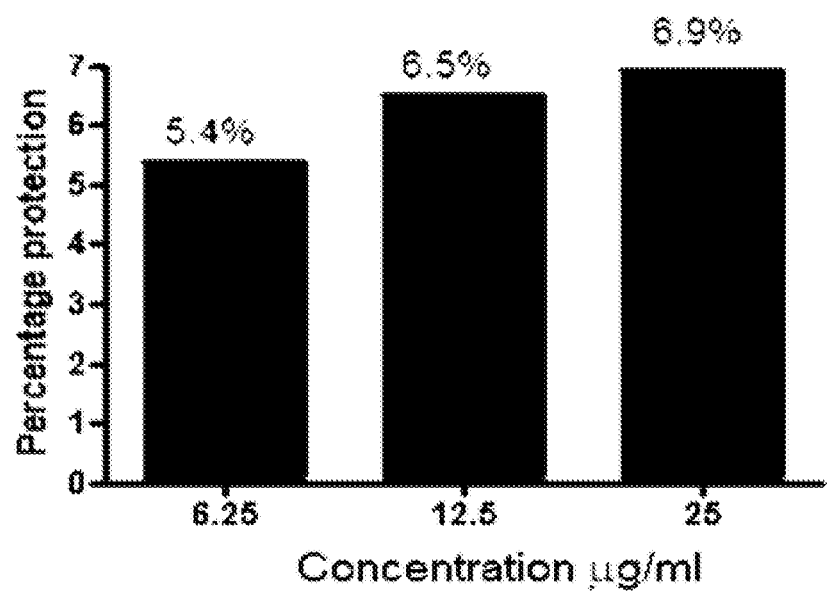
FIG. 5a is a graphical representation showing reduction of ROS induced by heavy metals using a composition comprising β-glucogallin.
Figure 5B:
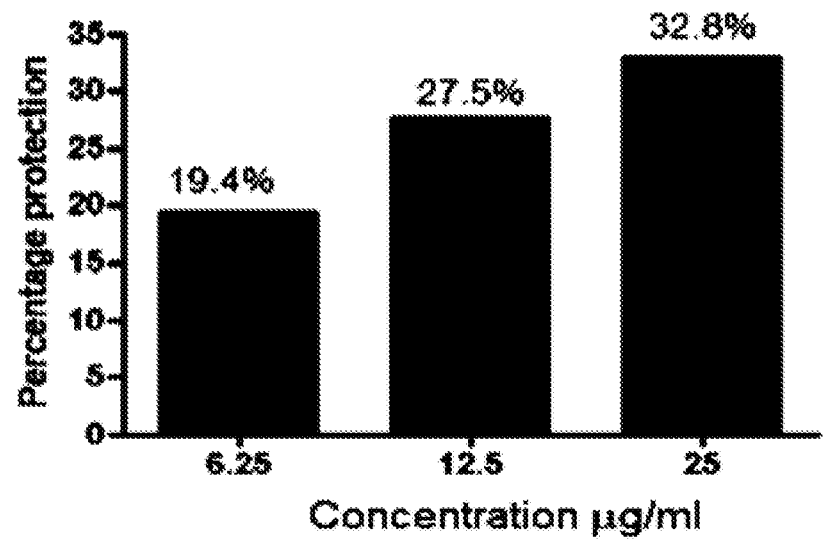
FIG. 5b is a graphical representation showing reduction of UVA-induced ROS using a composition comprising β-glucogallin.
Figure 5C:
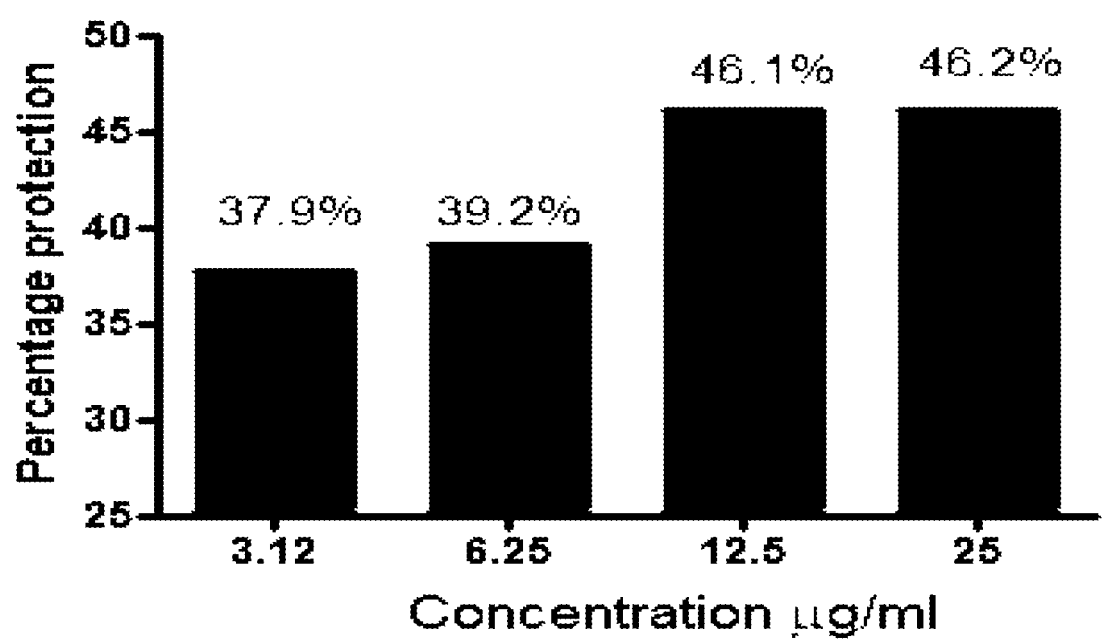
FIG. 5c is a graphical representation showing reduction of UVB-induced ROS using a composition comprising β-glucogallin.

The β-glucogallin composition at concentrations of 3.12-25 μg/ml, conferred a dose dependant protection against UVA+BaP (FIG. 4). Similarly, the composition reduced the ROS generated by exposure to heavy metals (FIG. 5a), UVA (FIG. 5b) and UVB (FIG. 5c).

Normalising Antioxidant Enzyme Activity

Figure 6A:
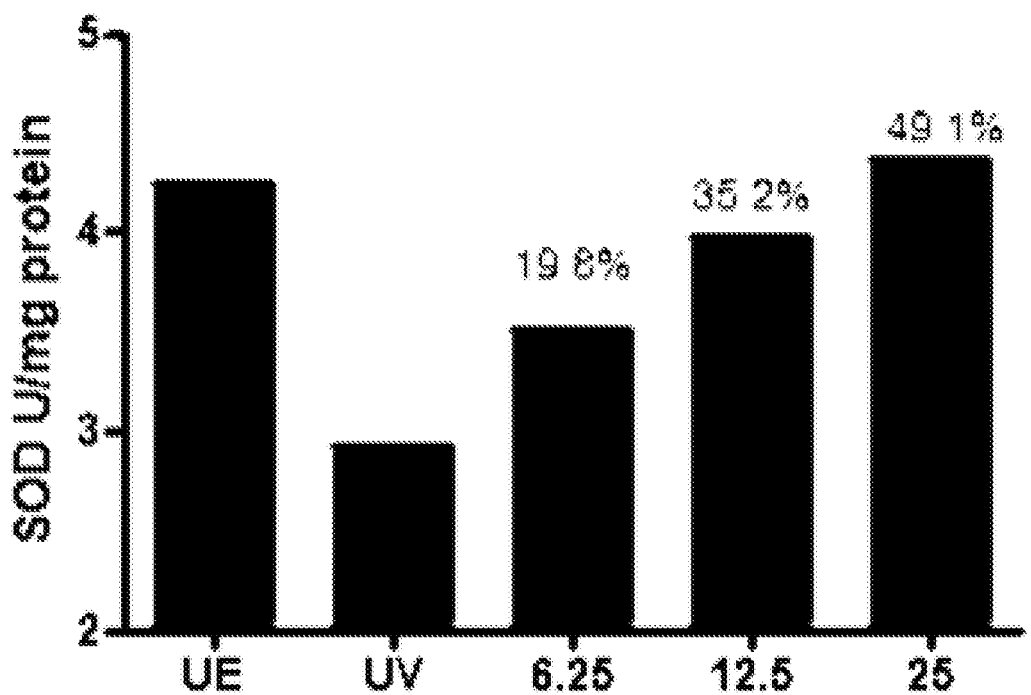
FIG. 6a is a graphical representation showing a dose dependant increase in superoxide dismutase activity by a composition comprising β-glucogallin. UE-Unexposed, UV-exposed
Figure 6B:
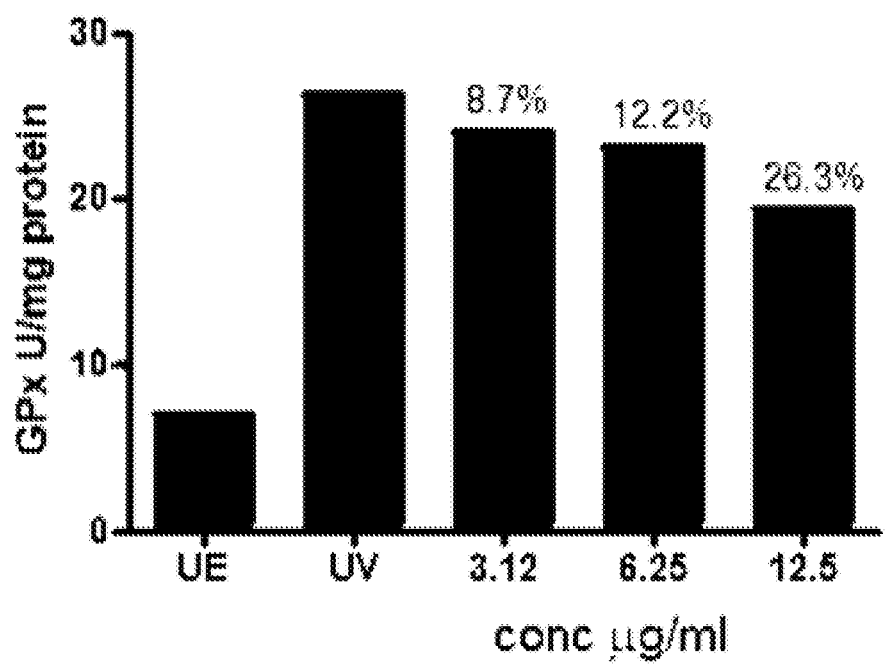
FIG. 6b is a graphical representation showing a dose dependant decrease in glutathione peroxidase activity by a composition comprising β-glucogallin. UE-Unexposed, UV-exposed

Exposure to UV reduced the superoxide dismutase concentrations and increased the glutathione peroxidase activity. The composition restored normal enzyme activity in Keratinocytes (FIGS. 6a and 6b)

Inhibition of Inflammatory Cytokines Induced by Pollutants

The β-glucogallin inhibited the production of IL-8, which is induced by the pollutants (Table 4)

TABLE 4

Inhibition of IL-8 by the β-glucogallin composition

| Concentration (μg/ml) | % inhibition of IL-8 |
|---|---|
| 12.5 | 5.16 |
| 25.00 | 14.13 |

Antioxidant Activity

The β-glucogallin composition exhibited excelled antioxidant activity by inhibiting the DPPH radical in a dose dependant manner with an IC50 of 4.34 μg/ml (Table 5).

TABLE 5

DPPH radical scavenging activity of the β-glucogallin composition

| Concentration (μg/ml) | % inhibition |
|---|---|
| 25.00 | 93.75 |
| 12.50 | 93.75 |
| 6.25 | 84.82 |
| 3.125 | 61.31 |
| 1.56 | 36.90 |
| IC50 | 4.34 (μg/ml) |

Anti Collagenase Activity

The β-glucogallin composition inhibited collagen degradation by inhibiting the enzyme collagenase (Table 6)

TABLE 6

Anti-collagenase activity of β-glucogallin composition

| Concentration (μg/ml) | % inhibition |
|---|---|
| 1000 | 47.78 |
| 500 | 28.38 |
| 250 | 16.87 |
| 125 | 13.66 |
| 62.5 | 6.25 |

Example 4: Anti-Pollution Effects of the 95% Tetrahydrocurcumin

Protection Against UVA and BaP

Figure 7:
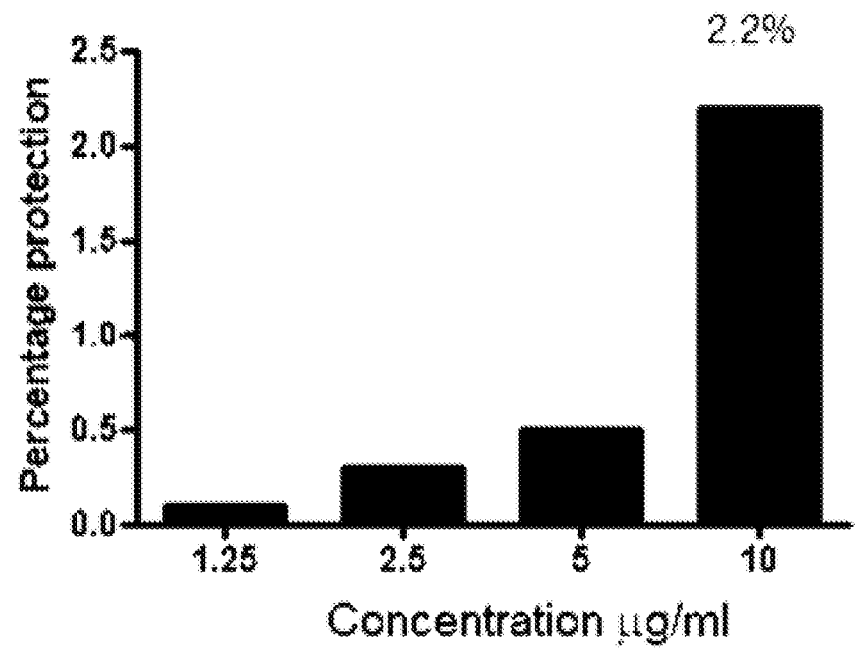
FIG. 7 is a graphical representation showing protection of Human HaCaT keratinocyte cells against UVA and BaP induced damage using 95% tetrahydrocurcumin.
Figure 8A:
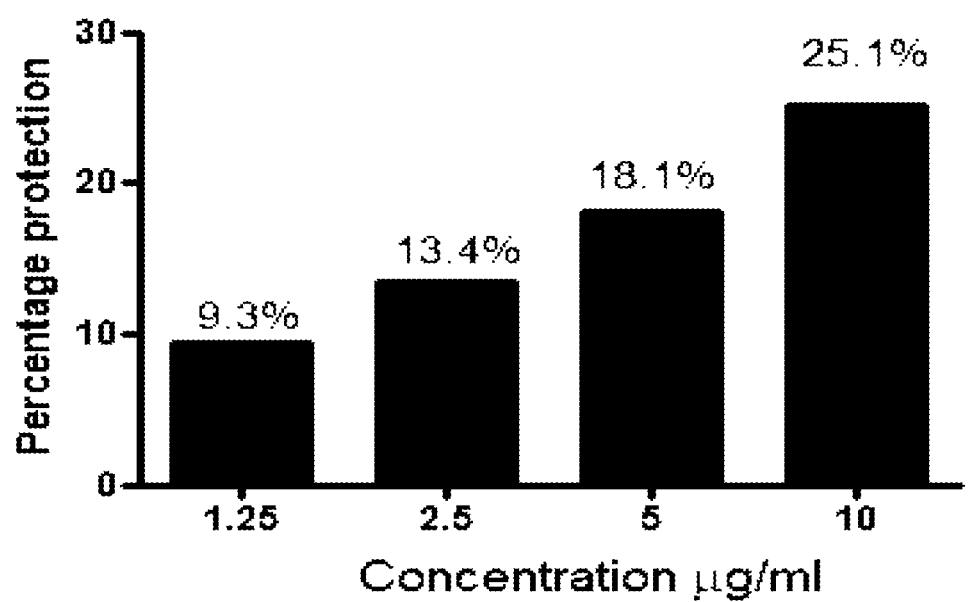
FIG. 8a is a graphical representation showing reduction of ROS induced by heavy metals using 95% tetrahydrocurcumin.
Figure 8B:
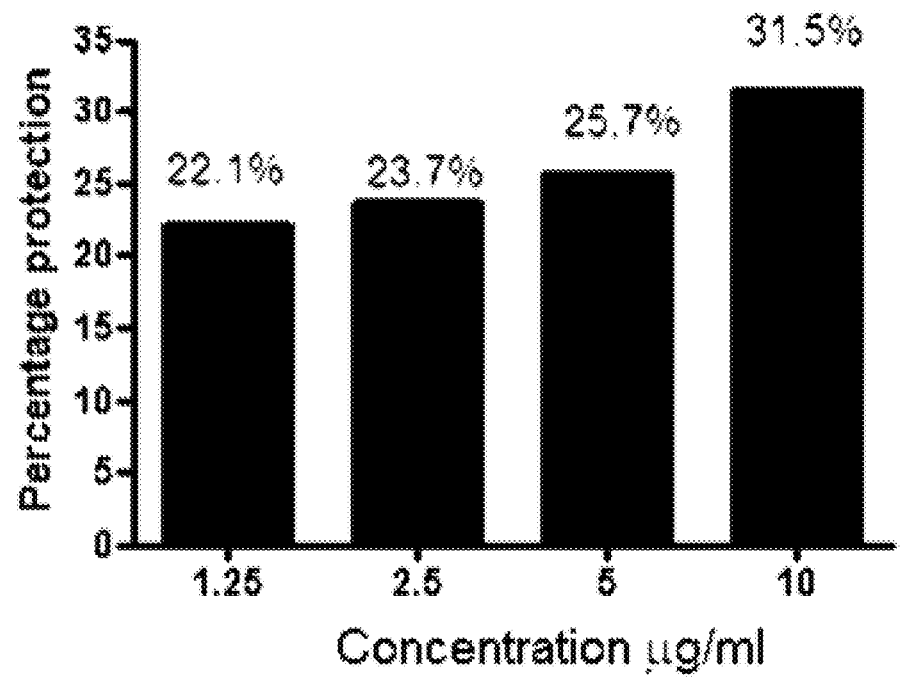
FIG. 8b is a graphical representation showing reduction of UVA-induced ROS using 95% tetrahydrocurcumin.
Figure 8C:
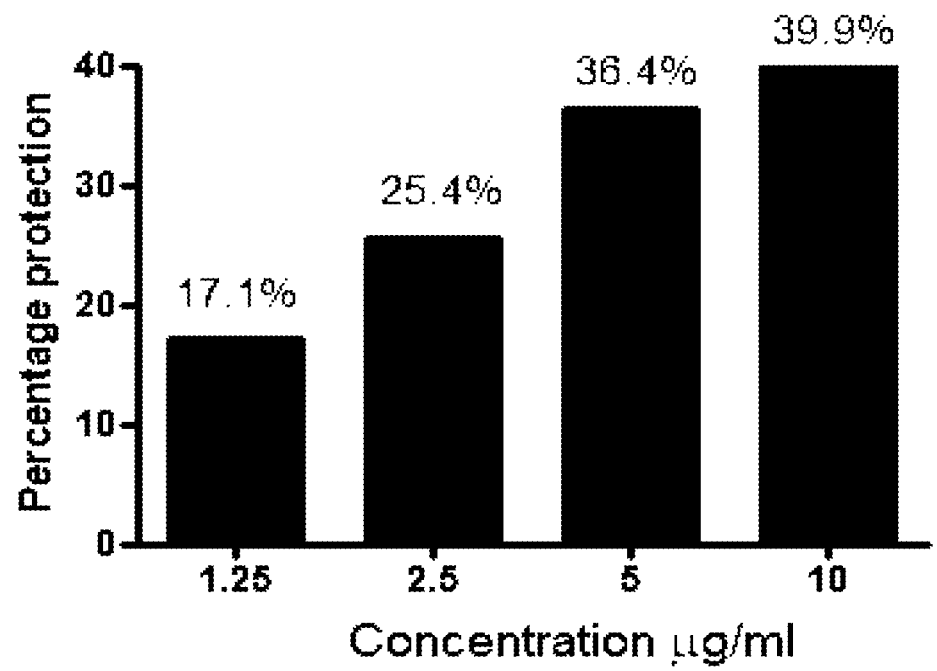
FIG. 8c is a graphical representation showing reduction of UVB-induced ROS using 95% tetrahydrocurcumin.

Tetrahydrocurucmin at concentrations of 1.25-10 μg/ml, conferred a dose dependant protection against UVA+BaP (FIG. 7). Similarly, the composition reduced the ROS generated by exposure to heavy metals (FIG. 8a), UVA (FIG. 8b) and UVB (FIG. 8c).

Normalising Antioxidant Enzyme Activity

Figure 9A:
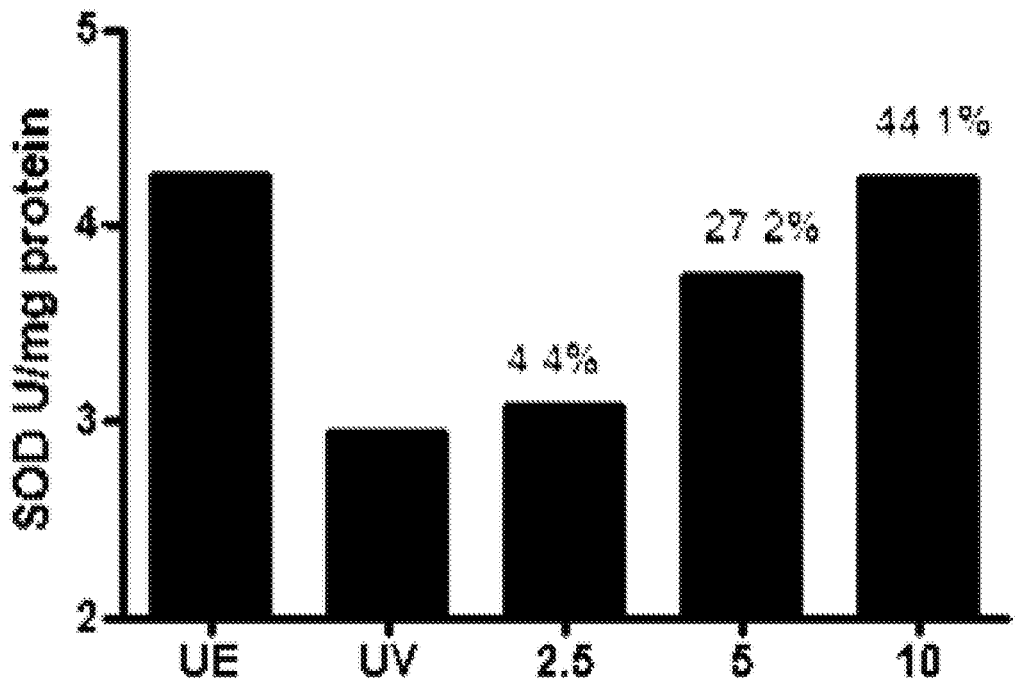
FIG. 9a is a graphical representation showing a dose dependant increase in superoxide dismutase activity by 95% tetrahydrocurcumin. UE-Unexposed, UV-exposed
Figure 9B:
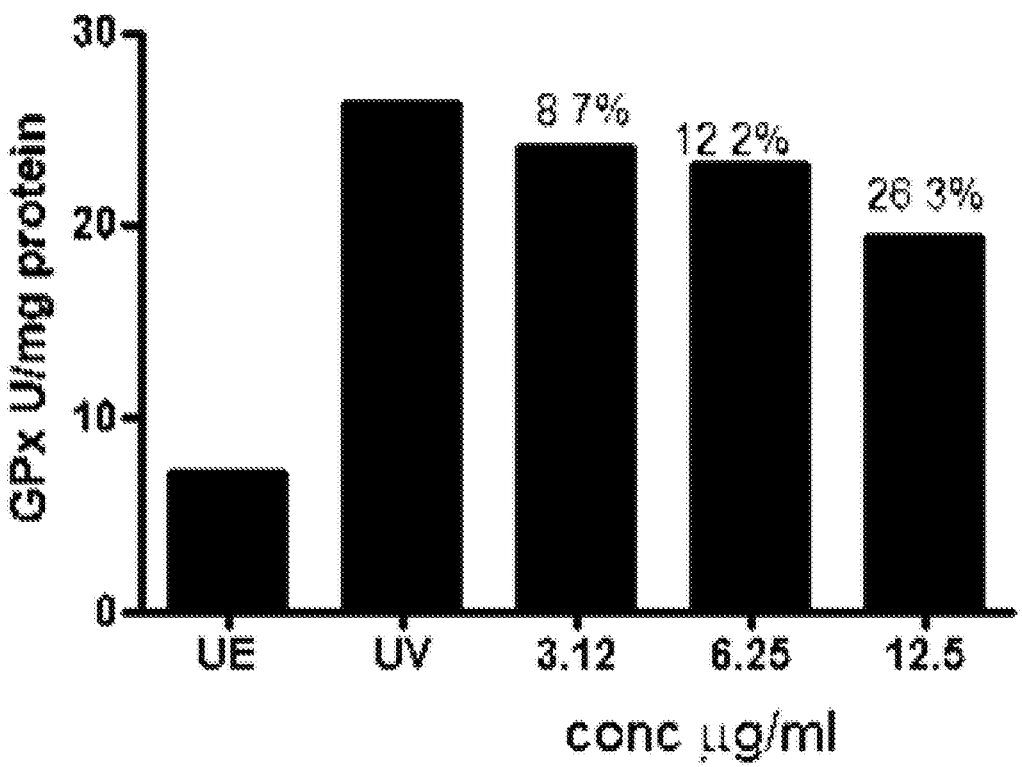
FIG. 9b is a graphical representation showing a dose dependant decrease in glutathione peroxidase activity by 95% tetrahydrocurcumin. UE-Unexposed, UV-exposed

Exposure to UV reduced the superoxide dismutase concentrations and increased the glutathione peroxidase activity. Tetrahydrocurucmin restored normal enzyme activity in Keratinocytes (FIGS. 9a and 9b)

Inhibition of Inflammatory Cytokines Induced by Pollutants

Tetrahydrocurucmin inhibited the production of IL-8, which is induced by the pollutants (Table 7)

TABLE 7

Inhibition of IL-8 by tetrahydrocurucmin

| Concentration (μg/ml) | % inhibition of IL-8 |
|---|---|
| 12.5 | 6.07 |
| 25.00 | 11.68 |

Antioxidant Activity

Tetrahydrocurucmin exhibited excelled antioxidant activity by inhibiting the DPPH radical in a dose dependant manner with an IC50 of 2.29 μg/ml (Table 8).

TABLE 8

DPPH radical scavenging activity of tetrahydrocurucmin

| Concentration (μg/ml) | % inhibition |
|---|---|
| 12.50 | 86.68 |
| 6.25 | 70.39 |
| 3.125 | 62.34 |
| 1.56 | 32.89 |
| 0.78 | 22.20 |
| IC50 | 2.29 (μg/ml) |

Anti Collagenase Activity

Tetrahydrocurucmin inhibited collagen degradation by inhibiting the enzyme collagenase (Table 9)

TABLE 9

Anti-collagenase activity of Tetrahydrocurucmin

| Concentration (μg/ml) | % inhibition |
|---|---|
| 500 | 16.10 |
| 250 | No activity |

Example 4: Anti-Pollution Effects of the 95% Oxyresveratrol

Protection Against UVA and BaP

Figure 10:
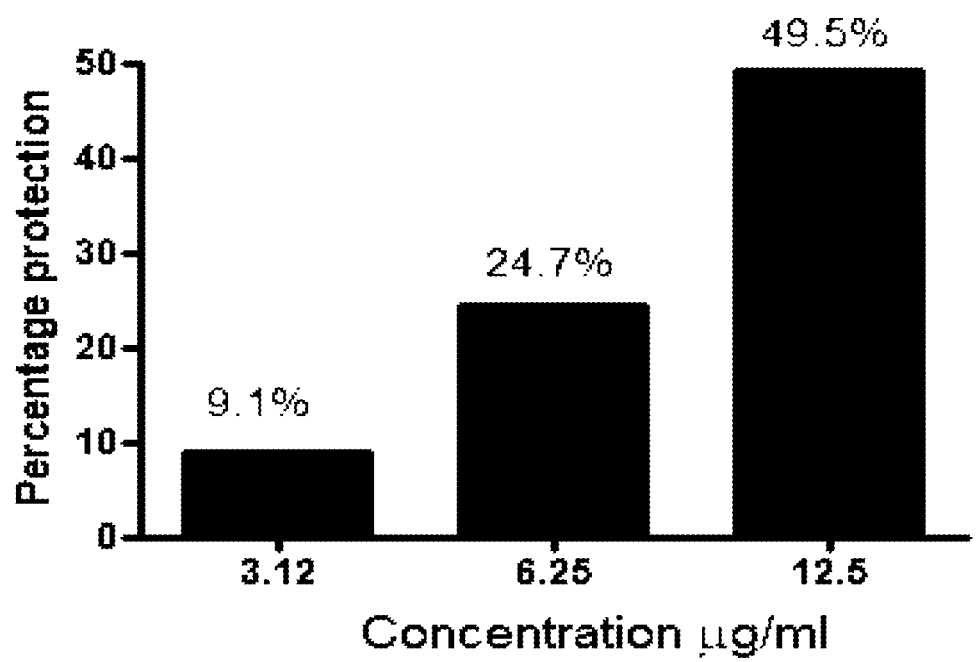
FIG. 10 is a graphical representation showing protection of Human HaCaT keratinocyte cells against UVA and BaP induced damage using 95% oxyresveratrol.
Figure 11A:
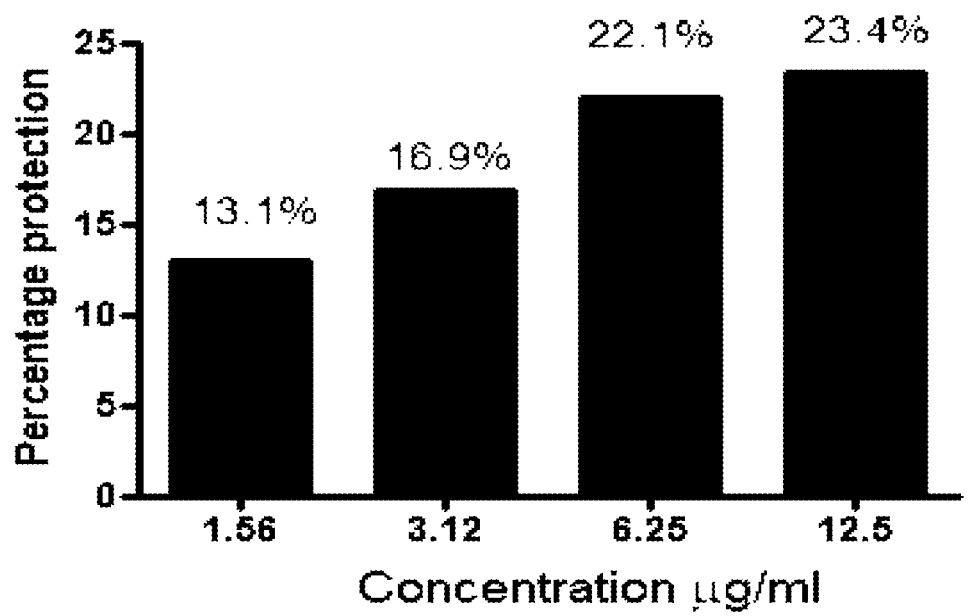
FIG. 11a is a graphical representation showing reduction of ROS induced by heavy metals using 95% oxyresveratrol.
Figure 11B:
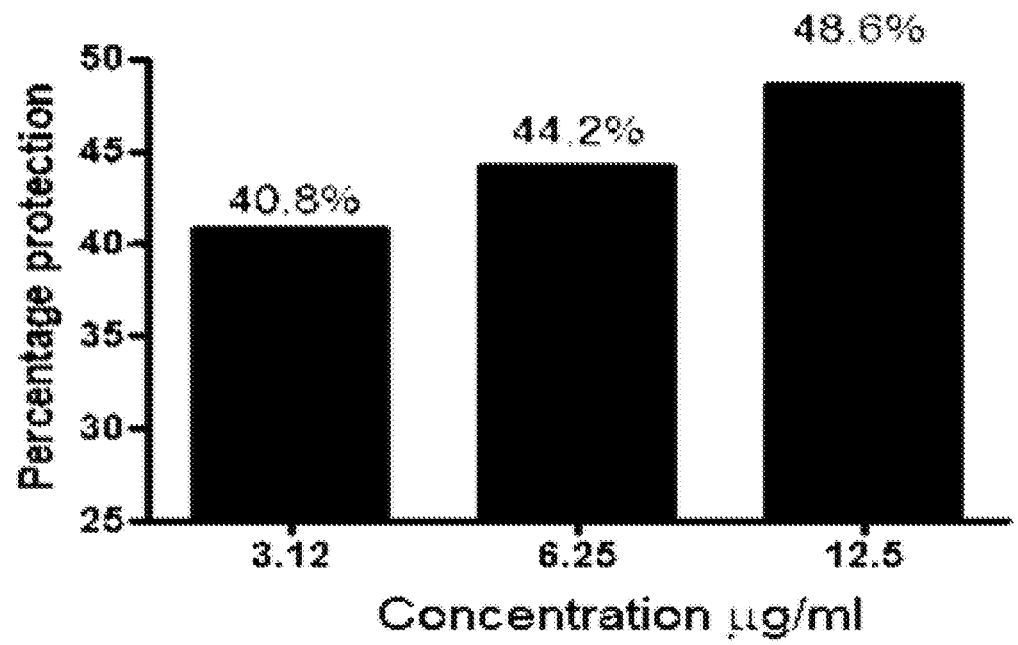
FIG. 11b is a graphical representation showing reduction of UVA-induced ROS using 95% oxyresveratrol.
Figure 11C:
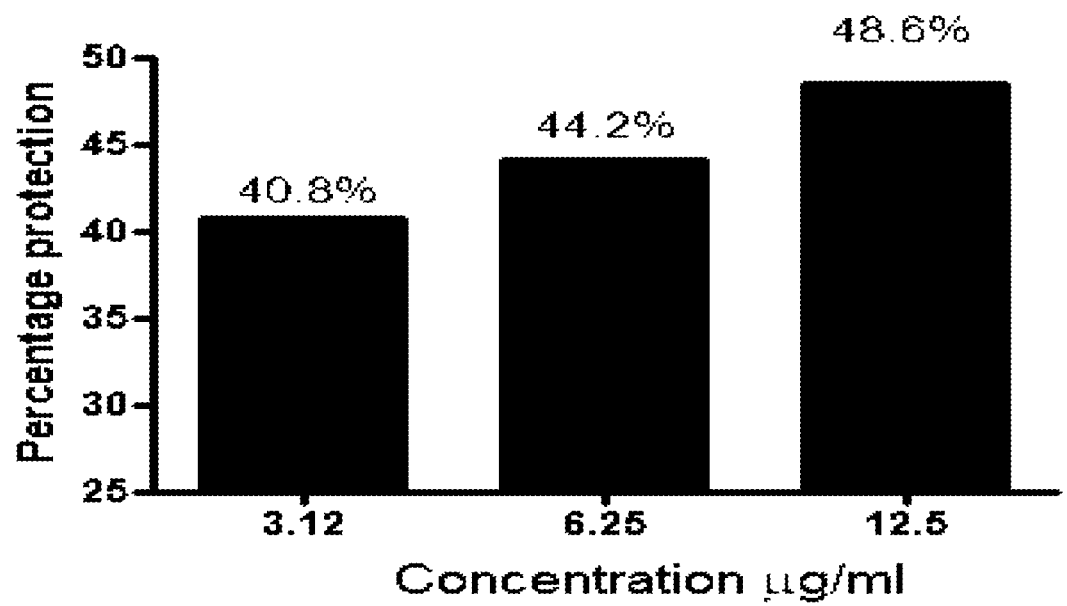
FIG. 11c is a graphical representation showing reduction of UVB-induced ROS using 95% oxyresveratrol.

Oxyresveratrol at concentrations of 3.12-12.5 μg/ml, conferred a dose dependant protection against UVA+BaP (FIG. 10). Similarly, the composition reduced the ROS generated by exposure to heavy metals (FIG. 11a), UVA (FIG. 11b) and UVB (FIG. 11c).

Normalising Antioxidant Enzyme Activity

Figure 12A:
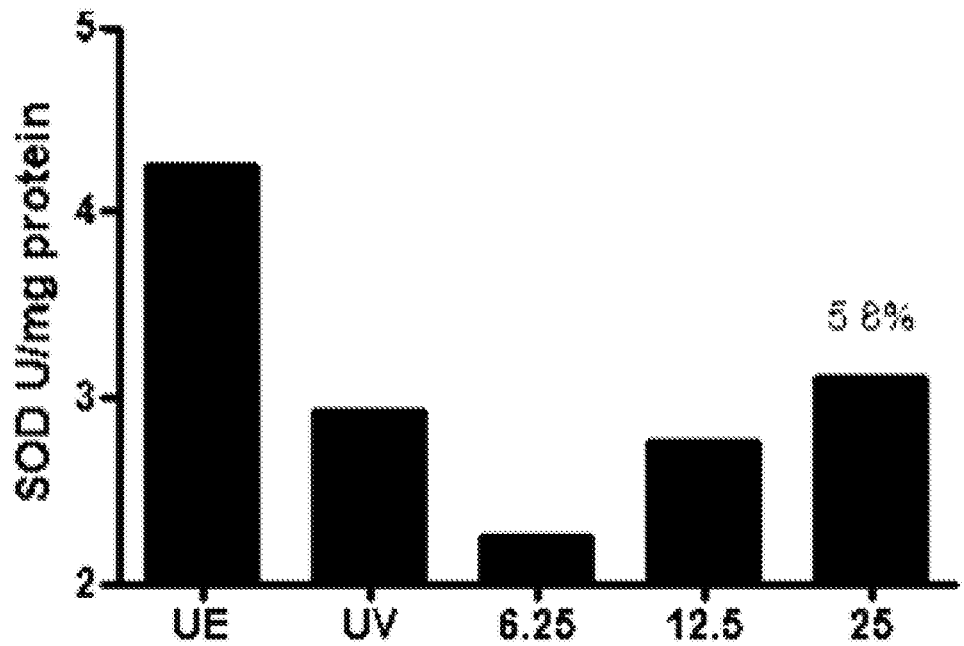
FIG. 12a is a graphical representation showing a dose dependant increase in superoxide dismutase activity by 95% oxyresveratrol. UE-Unexposed, UV-exposed
Figure 12B:
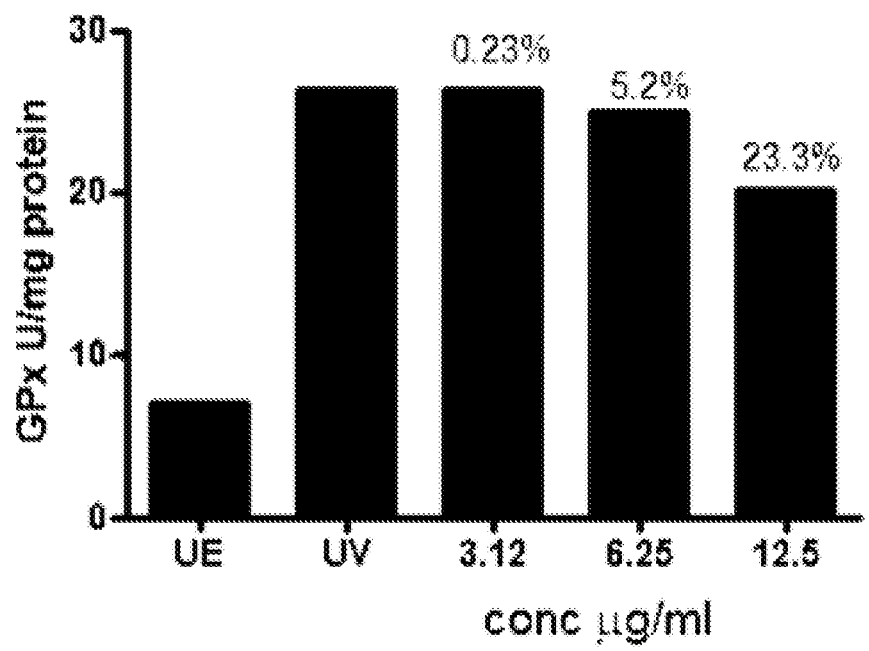
FIG. 12b is a graphical representation showing a dose dependant decrease in glutathione peroxidase activity by 95% oxyresveratrol. UE-Unexposed, UV-exposed

Exposure to UV reduced the superoxide dismutase concentrations and increased the glutathione peroxidase activity. Oxyresveratrol restored normal enzyme activity in Keratinocytes (FIGS. 12a and 12b)

Inhibition of Inflammatory Cytokines Induced by Pollutants

Oxyresveratrol inhibited the production of IL-8, which is induced by the pollutants (Table 10)

TABLE 10

Inhibition of IL-8 by Oxyresveratrol

| Concentration (μg/ml) | % inhibition of IL-8 |
|---|---|
| 3.125 | 13.27 |
| 6.25 | 18.36 |

Antioxidant Activity

Oxyresveratrol exhibited excelled antioxidant activity by inhibiting the DPPH radical in a dose dependant manner with an IC50 of 0.61 μg/ml (Table 11).

TABLE 11

DPPH radical scavenging activity of oxyresveratrol

| Concentration (μg/ml) | % inhibition |
|---|---|
| 5.00 | 84.14 |
| 2.5 | 77.89 |
| 1.25 | 68.63 |
| 0.625 | 42.07 |
| 0.3125 | 22.9 |
| IC50 | 0.61 (μg/ml) |

Anti Collagenase Activity

Oxyresveratrol inhibited collagen degradation by inhibiting the enzyme collagenase (Table 12).

TABLE 12

Anti-collagenase activity of Oxyresveratrol

| Concentration (μg/ml) | % inhibition |
|---|---|
| 100 | 80.92 |
| 50 | 41.19 |
| 25 | 9.93 |
| 12.5 | 0.05 |

Example 5: Anti-Pollution Effects of Combination of Bioactive Compositions

The combinatorial effects of the bioactive composition were evaluated by their ability to protect against UV A-Benzo (a) Pyrene in HaCaT cells. The results are tabulated below in table 13:

TABLE 13

Anti-pollution effects of combination of bioactive compositions

| Combination | % Protection against BaP |
|---|---|
| Oxyresveratrol (6.25 μg/ml)/Tetrahydrocurcumin (5 μg/ml) | 25.905 |
| Oxyresveratrol (6.25 μg/ml)/Oroxylin, baicalein, chrysin composition (12.5 μg/ml) | 143.89 |
| Oxyresveratrol (6.25 μg/ml)/Pterostilbene (2.5 μgml) | 24.42 |
| Oxyresveratrol (6.25 μg/ml)/β glucogallin composition (25 μg/ml) | 21.78 |
| Tetrahydrocurcumin (2.5 μg/ml)/Oroxylin, baicalein, chrysin composition (12.5 μg/ml) | 69.795 |
| Tetrahydrocurcumin (5 μg/ml)/Pterostilbene (2.5 μgml) | 3.11 |
| Tetrahydrocurcumin (5 μg/ml)/β glucogallin composition (25 μg/ml) | 11.37 |

TABLE 13-continued

Anti-pollution effects of combination of bioactive compositions

| Combination | % Protection against BaP |
|---|---|
| Oroxylin, baicalein, chrysin composition (12.5 μg/ml)/pterostilbene (2.5 μgml) | 75.405 |
| Oroxylin, baicalein, chrysin composition (12.5 μg/ml)/β glucogallin composition (25 μg/ml) | 61.215 |
| Pterostilbene (2.5 μgml)/β glucogallin composition (2.5 μg/ml) | 2.805 |

The activity of the individual actives are mentioned in table 14:

TABLE 14

| Active | % Protection against BaP |
|---|---|
| Oxyresveratrol (6.25 μg/ml) | 28.04 |
| Oroxylin, baicalein, chrysin composition (12.5 μg/ml) | 51.03 |
| β glucogallin composition (25 μg/ml) | 13.18 |
| Tetrahydrocurcumin (5 μg/ml) | No activity |
| Pterostilbene (2.5 μgml) | No activity |

The results indicate that combinations with Oroxylin, baicalein, chrysin composition showed synergistic activity and can be incorporated into formulations individually or in combination with other anti-pollution agents.

The composition comprising Oroxylin, baicalein, chrysin composition with different plant actives was further evaluated for their ability to protect against UVA-BaP exposure and UVA and heavy metal induced ROS scavenging. The results are tabulated in the following tables:

Protection Against UV-A BaP Exposure

TABLE 15

Protection against UV-A BaP using a combination comprising Oroxylin, baicalein, chrysin and oxyresveratrol

| Concentration (μg/ml) | | |
|---|---|---|
| Composition comprising Oroxylin, baicalein, chrysin | Oxyresveratrol | % Protection |
| 12.50 | 6.25 | 192.53 ± 8.08 |
| 6.25 | 3.13 | 146.52 ± 17.17 |
| 3.13 | 1.56 | 80.38 ± 1.78 |
| 1.56 | 0.78 | 35.97 ± 4.21 |

TABLE 16

Protection against UV-A BaP using a combination comprising Oroxylin, baicalein, chrysin and tetrahydrocurcumin

| Concentration (μg/ml) | | |
|---|---|---|
| Composition comprising Oroxylin, baicalein, chrysin | Tetrahydrocurcumin | % Protection |
| 12.50 | 5.00 | 112.79 ± 2.01 |
| 6.25 | 2.50 | 83.55 ± 1.91 |
| 3.13 | 1.25 | 51.21 ± 3.77 |

TABLE 17

Protection against UV-A BaP using a combination comprising Oroxylin, baicalein, chrysin and Pterostilbene Concentration (µg/ml)

| Composition comprising Oroxylin, baicalein, chrysin | Pterostilbene | % Protection |
|---|---|---|
| 12.50 | 2.50 | 80.57 ± 4.54 |
| 6.25 | 1.25 | 53.93 ± 0.15 |
| 3.13 | 0.63 | 32.28 ± 0.11 |
| 1.56 | 0.31 | 22.76 ± 0.93 |

TABLE 18

Protection against UV-A BaP using a combination comprising Oroxylin, baicalein, chrysin and β-glucogallin composition Concentration (µg/ml)

| Composition comprising Oroxylin, baicalein, chrysin | β-glucogallin composition | % Protection |
|---|---|---|
| 12.50 | 25.00 | 88.77 ± 7.69 |
| 6.25 | 12.50 | 98.09 ± 0.96 |
| 3.13 | 6.25 | 59.19 ± 6.51 |

Reduction in UVA Induced ROS

TABLE 19

Reduction in UV-A inducted ROS using a combination comprising Oroxylin, baicalein, chrysin and oxyresveratrol.

Concentration (µg/ml)

| Composition comprising Oroxylin, baicalein, chrysin | Oxyresveratrol | % Protection |
|---|---|---|
| 12.50 | 6.25 | 61.94 ± 1.09 |
| 6.25 | 3.13 | 56.23 ± 1.90 |
| 3.13 | 1.56 | 47.52 ± 1.49 |
| 1.56 | 0.78 | 30.19 ± 1.29 |
| 0.78 | 0.39 | 17.26 ± 2.43 |

TABLE 20

Reduction in UV-A inducted ROS using a combination comprising Oroxylin, baicalein, chrysin and tetrahydrocurcumin.

Concentration (µg/ml)

| Composition comprising Oroxylin, baicalein, chrysin | Tetrahydrocurcumin | % Protection |
|---|---|---|
| 12.50 | 5.00 | 46.73 ± 0.36 |
| 6.25 | 2.50 | 39.02 ± 1.89 |
| 3.13 | 1.25 | 34.27 ± 0.58 |
| 1.56 | 0.63 | 22.76 ± 3.57 |
| 0.78 | 0.31 | 11.11 ± 0.35 |

TABLE 21

Reduction in UV-A inducted ROS using a combination comprising Oroxylin, baicalein, chrysin and pterostilbene.

Concentration (µg/ml)

| Composition comprising Oroxylin, baicalein, chrysin | Pterostilbene | % Protection |
|---|---|---|
| 12.50 | 2.50 | 50.63 ± 1.92 |
| 6.25 | 1.25 | 32.54 ± 1.39 |
| 3.13 | 0.63 | 14.37 ± 0.37 |
| 1.56 | 0.31 | 3.0 ± 7.1 |
| 0.78 | 0.16 | 3.02 ± 2.9 |

TABLE 22

Reduction in UV-A inducted ROS using a combination comprising Oroxylin, baicalein, chrysin and β-glucogallin composition.

Concentration (µg/ml)

| Composition comprising Oroxylin, baicalein, chrysin | β-glucogallin composition | % Protection |
|---|---|---|
| 12.50 | 25.00 | 34.48 ± 9.77 |
| 6.25 | 12.50 | 21.76 ± 9.40 |
| 3.13 | 6.25 | 35.91 ± 0.56 |
| 1.56 | 3.13 | 28.58 ± 1.84 |
| 0.78 | 1.56 | 23.47 ± 6.55 |

TABLE 23

Reduction in heavy metal inducted ROS using a combination comprising Oroxylin, baicalein, chrysin and β-glucogallin composition.

Concentration (µg/ml)

| Composition comprising Oroxylin, baicalein, chrysin | β-glucogallin composition | % Protection |
|---|---|---|
| 12.50 | 25.00 | 62.56 ± 1.18 |
| 6.25 | 12.50 | 52.25 ± 0.92 |
| 3.13 | 6.25 | 38.65 ± 1.17 |
| 1.56 | 3.13 | 27.02 ± 4.44 |

TABLE 24

Reduction in heavy metal inducted ROS using a combination comprising Oroxylin, baicalein, chrysin and oxyresveratrol.

Concentration (µg/ml)

| Composition comprising Oroxylin, baicalein, chrysin | oxyresveratrol | % Protection |
|---|---|---|
| 12.50 | 6.25 | 68.08 ± 0.58 |
| 6.25 | 3.13 | 60.18 ± 2.62 |
| 3.13 | 1.56 | 54.16 ± 1.54 |
| 1.56 | 0.78 | 29.49 ± 3.31 |
| 0.78 | 0.39 | 13.30 ± 2.74 |

TABLE 25

Reduction in heavy metal inducted ROS using a combination comprising Oroxylin, baicalein, chrysin and tetrahydrocurcumin

| Concentration (μg/ml) | | |
|---|---|---|
| Composition comprising Oroxylin, baicalein, chrysin | tetrahydrocurcumin | % Protection |
| 12.50 | 5.00 | 62.39 ± 1.48 |
| 6.25 | 2.50 | 56.64 ± 4.71 |
| 3.13 | 1.25 | 46.41 ± 2.58 |
| 1.56 | 0.63 | 30.17 ± 13.07 |

TABLE 26

Reduction in heavy metal inducted ROS using a combination comprising Oroxylin, baicalein, chrysin and pterostilbene

| Concentration (μg/ml) | | |
|---|---|---|
| Composition comprising Oroxylin, baicalein, chrysin | Pterostilbene | % Protection |
| 12.50 | 2.50 | 58.21 ± 1.40 |
| 6.25 | 1.25 | 50.55 ± 0.69 |
| 3.13 | 0.63 | 36.02 ± 2.44 |
| 1.56 | 0.31 | 27.94 ± 1.88 |
| 0.78 | 0.16 | 13.15 ± 0.56 |

The results indicated that composition comprising Oroxylin, baicalein, chrysin composition with different plant actives synergistic increase in their ability to protect against UVA-BaP exposure and UVA and heavy metal induced ROS scavenging.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method for protecting mammalian skin against the harmful effects of UV radiation and environmental pollutants, said method comprising a step of topically administering to the mammalian skin in need thereof, a composition comprising not less than 10% w/w oroxylin A, not less than 10% w/w baicalein, not less than 2% w/w chrysin, and one or more ingredients selected from the group consisting of 95% w/w oxyresveratrol, 95% w/w tetrahydrocurcumin, and 90% w/w pterostilbene, wherein the composition protects the mammalian skin against UVA and benzo(a)pyrene (BaP).

2. The method as in claim 1, wherein the environmental pollutants are selected from the group consisting of particulate matter, polycyclic aromatic hydrocarbons, volatile organic compounds, detergents, nitrogen and sulfur oxides, carbon monoxide, ozone, and heavy metals.

3. The method as in claim 1, wherein the composition confers skin protection by increasing the levels of anti-oxidant enzymes and decreasing ROS levels and reducing levels of inflammatory markers.

4. The method as in claim 3, wherein the antioxidant enzymes are selected from the group consisting of glutathione peroxidase, superoxide dismutase and catalase.

5. The method as in claim 3, wherein the inflammatory markers are selected from the group consisting of interleukin (IL)-1alpha, IL-1beta, tumor necrosis factor (TNF)-alpha and IL-8.

6. The method as in claim 3, wherein the inflammatory marker is IL-8.

7. A method for cleansing and rejuvenating mammalian skin, exposed to environmental pollutants and UV radiation, said method comprising a step of topically administering to the mammalian skin in need thereof, a composition comprising not less than 10% w/w oroxylin A, not less than 10% w/w baicalein, not less than 2% w/w chrysin, and one or more ingredients selected from the group consisting of 95% w/w oxyresveratrol, 95% w/w tetrahydrocurcumin, and 90% w/w pterostilbene, wherein the composition protects the mammalian skin against UVA and benzo(a)pyrene (BaP).

8. The method as in claim 7, wherein the environmental pollutants are selected from the group consisting of particulate matter, polycyclic aromatic hydrocarbons, volatile organic compounds, detergents, nitrogen and sulfur oxides, carbon monoxide, ozone, and heavy metals.

9. The method as in claim 7, wherein the composition confers skin protection by decreasing collagenase activity, increasing the levels of anti-oxidant enzymes and decreasing ROS levels and reducing levels of inflammatory markers.

10. The method as in claim 9, wherein the antioxidant enzymes are selected from the group consisting of glutathione peroxidase, superoxide dismutase and catalase.

11. The method as in claim 9, wherein the inflammatory markers are selected from the group consisting of interleukin (IL)-1alpha, IL-1beta, tumor necrosis factor (TNF)-alpha and IL-8.

12. The method as in claim 9, wherein the inflammatory marker is IL-8.

13. The method as in claim 1, wherein the composition comprises not less than 10% w/w oroxylin A, not less than 10% w/w baicalein, not less than 2% w/w chrysin, and 95% w/w oxyresveratrol.

14. The method as in claim 1, wherein the composition comprises not less than 10% w/w oroxylin A, not less than 10% w/w baicalein, not less than 2% w/w chrysin, and 95% w/w tetrahydrocurcumin.

15. The method as in claim 1, wherein the composition comprises not less than 10% w/w oroxylin A, not less than 10% w/w baicalein, not less than 2% w/w chrysin, and 90% w/w pterostilbene.

16. The method as in claim 7, wherein the composition comprises not less than 10% w/w oroxylin A, not less than 10% w/w baicalein, not less than 2% w/w chrysin, and 95% w/w oxyresveratrol.

17. The method as in claim 7, wherein the composition comprises not less than 10% w/w oroxylin A, not less than 10% w/w baicalein, not less than 2% w/w chrysin, and 95% w/w tetrahydrocurcumin.

18. The method as in claim 7, wherein the composition comprises not less than 10% w/w oroxylin A; not less than 10% w/w baicalein, not less than 2% w/w chrysin, and 90% w/w pterostilbene.

* * * * *